(12) United States Patent
Imaizumi et al.

(10) Patent No.: US 12,380,573 B2
(45) Date of Patent: Aug. 5, 2025

(54) TAXIS ANALYSIS METHOD, CANCER EVALUATION METHOD, TAXIS ANALYSIS SYSTEM AND PROGRAM

(71) Applicant: HIROTSU BIO SCIENCE INC., Chiyoda-ku (JP)

(72) Inventors: Yuki Imaizumi, Ehime (JP); Kenji Iwao, Ehime (JP)

(73) Assignee: HIROTSU BIO SCIENCE INC., Chiyoda-ku (JP)

( * ) Notice: Subject to any disclaimer, the term of this patent is extended or adjusted under 35 U.S.C. 154(b) by 343 days.

(21) Appl. No.: 17/781,898

(22) PCT Filed: Dec. 3, 2020

(86) PCT No.: PCT/JP2020/044989
§ 371 (c)(1),
(2) Date: Jun. 2, 2022

(87) PCT Pub. No.: WO2021/112162
PCT Pub. Date: Jun. 10, 2021

(65) Prior Publication Data
US 2023/0020220 A1 Jan. 19, 2023

(30) Foreign Application Priority Data
Dec. 6, 2019 (JP) .................. 2019-221268

(51) Int. Cl.
*G06T 7/20* (2017.01)
*G06T 7/73* (2017.01)

(52) U.S. Cl.
CPC .................. *G06T 7/20* (2013.01); *G06T 7/74* (2017.01); *G06T 2207/30096* (2013.01)

(58) Field of Classification Search
None
See application file for complete search history.

(56) References Cited

U.S. PATENT DOCUMENTS

| | | |
|---|---|---|
| RE49,311 E | 11/2022 | Van Der Lelie et al. |
| 2017/0016906 A1 | 1/2017 | Hirotsu et al. |

(Continued)

FOREIGN PATENT DOCUMENTS

| | | |
|---|---|---|
| AU | 2017323139 A1 | 5/2019 |
| CN | 106290169 A | 1/2017 |

(Continued)

OTHER PUBLICATIONS

International Search Report issued Feb. 22, 2021 in PCT/JP2020/044989, filed on Dec. 3, 2020, 3 pages.

(Continued)

*Primary Examiner* — Vikkram Bali
(74) *Attorney, Agent, or Firm* — Oblon, McClelland, Maier & Neustadt, L.L.P.

(57) ABSTRACT

A taxis analysis method for performing taxis analysis of nematodes using a container in which a reference point is provided in the container or a culture medium in the container, the taxis analysis method including steps of: imaging a distribution mode of the nematodes in the container after the nematodes and a specimen of a subject are dropped into the container; detecting a position of an object of the reference point corresponding to the reference point included in the image obtained by imaging; determining an attraction region and a avoidance region on the basis of the position; and executing taxis analysis using objects of the nematodes in the determined attraction region and avoidance region.

10 Claims, 23 Drawing Sheets

(56) References Cited

U.S. PATENT DOCUMENTS

| | | | |
|---|---|---|---|
| 2017/0044476 A1* | 2/2017 | Madsen | C12M 21/06 |
| 2018/0092363 A1 | 4/2018 | Van Der Lelie et al. | |
| 2018/0313839 A1 | 11/2018 | Sakairi et al. | |
| 2019/0079071 A1 | 3/2019 | Sakairi et al. | |
| 2019/0369084 A1 | 12/2019 | Hirotsu et al. | |

FOREIGN PATENT DOCUMENTS

| | | | |
|---|---|---|---|
| CN | 110087460 A | | 8/2019 |
| JP | 2002-527148 | * | 8/2002 |
| JP | 2018-61515 A | | 4/2018 |
| JP | 2019-532956 A | | 11/2019 |
| TW | 201812627 A | | 4/2018 |
| WO | WO 00/21590 A1 | | 4/2000 |
| WO | WO 2016/147268 A1 | | 9/2016 |
| WO | WO 2017/081750 A1 | | 5/2017 |
| WO | WO 2017/094066 A1 | | 6/2017 |
| WO | WO 2017/150569 A1 | | 9/2017 |
| WO | WO 2018/029882 A1 | | 2/2018 |
| WO | WO 2018/047959 A1 | | 3/2018 |

OTHER PUBLICATIONS

Hirotsu et al. "A Highly Accurate Inclusive Cancer Screening Test Using Caenorhabditis elegans Scent Detection", Plos One, Mar. 11, 2015, pp. 1-15.

Taiwanese Office Action issued Mar. 25, 2024 in Taiwanese Patent Application No. 109142594, 16 pages.

Extended European Search Report issued Dec. 12, 2023 in European Patent Application No. 20896568.1, 9 pages.

Bilbao, A., "Navigation of *C. elegans* in three-dimensional media: roll maneuvers and planar turns," Physics.bio-ph, Sep. 12, 2016, XP081152047, 14 pages.

Office Action issued May 31, 2025, in corresponding Chinese Patent Application No. 202080080211.4, citing documents 15 and 16 therein, 7 pages.

* cited by examiner

FIG.6

| SUBJECT ID | PETRI DISH ID | STATIONARY START DATE AND TIME | STATIONARY END DATE AND TIME | TEMPERATURE | IMAGING ID | NUMBER OF ATTRACTED NEMATODES | NUMBER OF REPELLED NEMATODES | TAXIS INDEX | CANCER EVALUATION RESULT |
|---|---|---|---|---|---|---|---|---|---|
| 00000001 | 12345678 | 20190505 1200 | 20190505 1300 | 23.0 | 12345678 | 20 | 40 | -0.33 | 0 |
| ... | ... | ... | ... | ... | ... | ... | ... | ... | ... |

T1

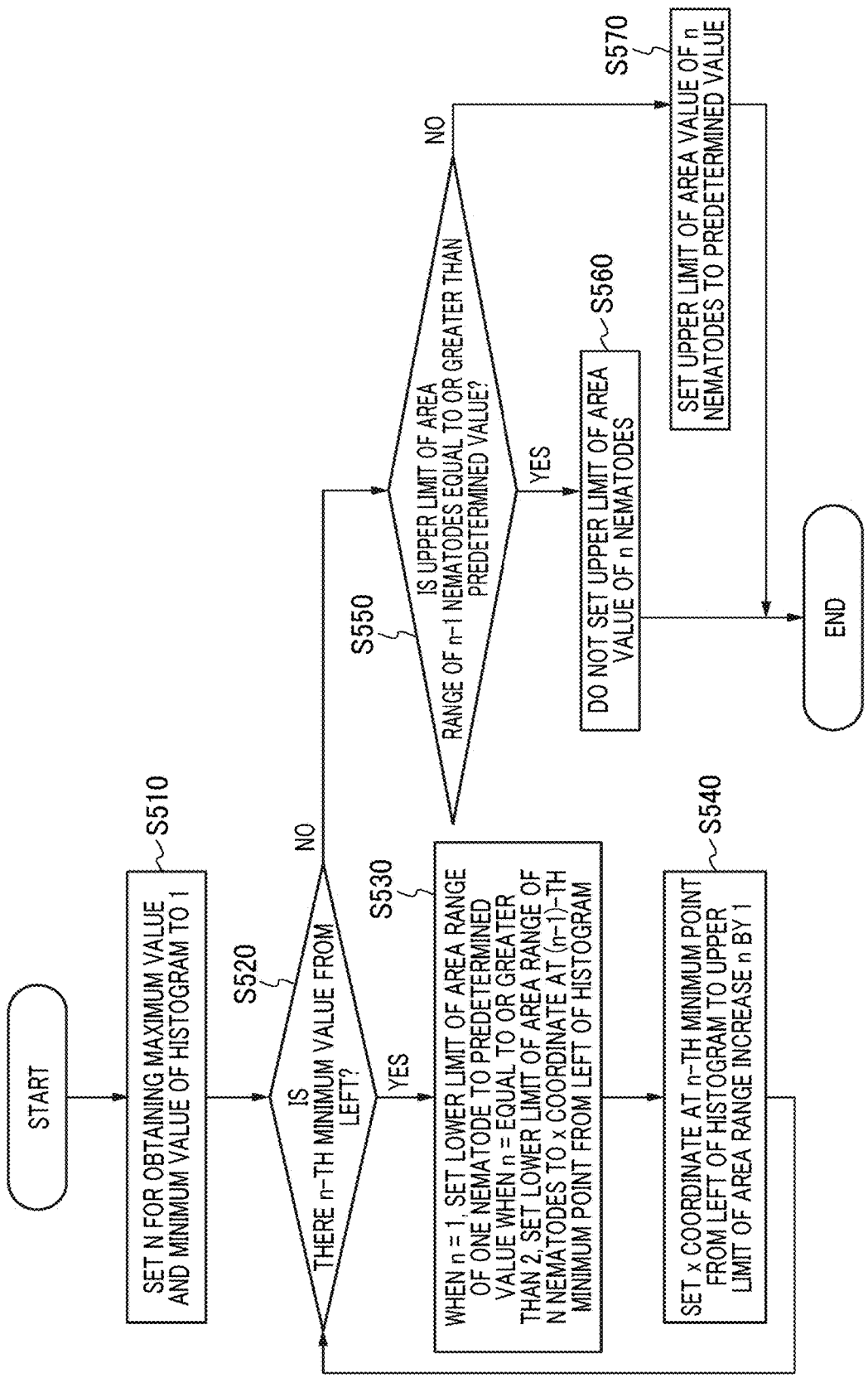

TAXIS ANALYSIS METHOD, CANCER EVALUATION METHOD, TAXIS ANALYSIS SYSTEM AND PROGRAM

TECHNICAL FIELD

The present invention relates to a taxis analysis method, a cancer evaluation method, a taxis analysis system and a program.

BACKGROUND ART

In the related art, a cancer detection method using taxis of nematodes that exhibit attraction behavior with respect to urine of a cancer patient is known (see, for example, Non Patent Literature 1.).

CITATION LIST

Non Patent Literature

Non-Patent Literature 1: Hirotsu T. et al., PLOS ONE, 10 (3): e 0118699, 2015

SUMMARY OF INVENTION

Technical Problem

Processing of a large number of urine samples with the technique of Non Patent Literature 1 requires automation by a machine. It is conceivable to analyze taxis of nematodes by dropping a urine sample into a culture medium in a container (for example, a Petri dish), placing the nematodes on the culture medium, moving the sample to below an imaging device after a predetermined time has elapsed and imaging the nematodes in the culture medium with the imaging device. In this case, the container may rotate in association with movement of the container. For this reason, if the container has a point-symmetric or line-symmetric shape, there is a problem that it is not possible to specify a place where the urine sample is dropped in the container from an image obtained by the imaging, and it is not possible to determine whether the nematodes exhibit attraction behavior.

The present invention has been made in view of the above problem, and it is an object of the present invention to provide a taxis analysis method, a cancer evaluation method, a taxis analysis system and a program capable of determining whether nematodes exhibit attraction behavior from an image obtained by imaging even when a container on which the nematodes are placed has a point-symmetrical or line-symmetrical shape.

Solution to Problem

A taxis analysis method according to a first aspect of the present invention, the taxis analysis method for performing taxis analysis of nematodes using a container in which a reference point is provided in the container or a culture medium in the container, the taxis analysis method comprises steps of:
 imaging a distribution mode of the nematodes in the container;
 determining an attraction region and/or a avoidance region based on the reference point; and
 executing taxis analysis using objects of nematodes in the determined attraction region and/or avoidance region.

According to this configuration, the attraction region and the avoidance region can be correctly set with reference to the position of the object of the reference point corresponding to the reference point even if the container is imaged at any rotation angle from a position facing a bottom surface, so that it is possible to correctly perform taxis analysis of the nematodes even if the container is imaged at any rotation angle from the position facing the bottom surface.

A taxis analysis method according to a second aspect of the present invention, the taxis analysis method according to the first aspect of the taxis analysis method, wherein in the step of executing the taxis analysis, the nematodes in the determined attraction region are counted and/or the nematodes in the determined avoidance region are counted, and a taxis analysis result is output according to a count result.

According to this configuration, a taxis analysis result can be output even if the container is imaged at any rotation angle from the position facing the bottom surface.

A taxis analysis method according to a third aspect of the present invention, the taxis analysis method according to the first or the second aspect of the taxis analysis method,
 wherein the reference point is a code including container identification information for identifying the container,
 an image obtained in the step of imaging includes a code object corresponding to the code, and
 the taxis analysis method further comprises steps of:
 reading the container identification information from the code object; and
 storing in a storage a taxis analysis result that is a result of executing the taxis analysis in association with the read container identification information.

According to this configuration, container identification information and the taxis analysis result can be managed in association with each other, and thus, if a subject and the container identification information are managed in advance in association with each other, the subject and the taxis analysis result can be specified from the container identification information, so that it is possible to reduce a possibility of misidentifying the taxis analysis result of the subject.

A taxis analysis method according to a forth aspect of the present invention, the taxis analysis method according to the third aspect of the taxis analysis method,
 wherein subject identification information for identifying a subject and container identification information are stored in the storage in association with each other, and
 the taxis analysis method further comprises a step of:
 identifying subject identification information corresponding to the container identification information read from the code object with reference to the storage.

According to this configuration, the subject can be specified from the container identification information, so that it is possible to reduce a possibility of misidentifying the taxis analysis result of the subject.

A taxis analysis method according to a fifth aspect of the present invention, the taxis analysis method according to the first of the second aspect of the taxis analysis method,
 wherein the reference point includes a first reference point and/or a second reference point.

According to this configuration, the attraction region and the avoidance region can be determined with reference to a first reference point and/or a second reference point.

A taxis analysis method according to a sixth aspect of the present invention, the taxis analysis method according to any one of the first to the fifth aspect of the taxis analysis method, further comprises a step of:

removing a lid of the container before imaging inside of the container.

According to this configuration, imaging is performed after a lid of the container is removed, so that it is possible to grasp distribution of nematodes with high accuracy and improve accuracy of taxis analysis.

A taxis analysis method according to a seventh aspect of the present invention, the taxis analysis method according to any one of the first to the sixth aspect of the taxis analysis method, wherein in the step of determining the attraction region and/or the avoidance region, an angle of a straight line passing through a position of an object of the reference point and a center of an object of the container with respect to a reference line is determined, and a reference format in which the attraction region and/or the avoidance region is set in advance is rotated by the angle to determine the attraction region and/or the avoidance region.

According to this configuration, it is possible to determine an appropriate attraction region and/or avoidance region without manual operation.

A taxis analysis method according to an eighth aspect of the present invention, the taxis analysis method according to any one of the first to the six aspect of the present invention, wherein in the step of determining the attraction region and/or the avoidance region, an angle of a straight line passing through a position of an object of the reference point and a center of an object of the container with respect to a reference line is determined, and an image obtained by the imaging is rotated by the angle to determine the attraction region and/or the avoidance region in the rotated image.

According to this configuration, it is possible to determine an appropriate attraction region and/or avoidance region without manual operation.

A taxis analysis method according to a ninth aspect of the present invention, the taxis analysis method for performing taxis analysis of nematodes using a container in which a reference point is provided in the container or a culture medium in the container, the taxis analysis method comprises steps of:

positioning the reference point and an imaging device in a predetermined positional relationship;

imaging a distribution mode of the nematodes in the container by the imaging device;

determining an attraction region and/or a avoidance region; and executing taxis analysis using objects of nematodes in the determined attraction region and/or avoidance region.

According to this configuration, orientation and a position of the container are always the same in an image obtained by imaging, which eliminates the need to correct positions of the attraction region and the avoidance region in the image obtained by imaging, so that it is possible to correctly perform taxis analysis of the nematodes.

A taxis analysis method according to a tenth aspect of the present invention, the taxis analysis method according to any one of the first to the sixth aspect of the taxis analysis method, wherein in the step of determining the attraction region and/or the avoidance region, an angle of a straight line passing through a position of an object of the reference point and a center of an object of the container with respect to a reference line is determined, the container is rotated by the angle, a distribution mode of the nematodes in the container after the rotation is imaged, and the attraction region and/or the avoidance region is determined by comparing an image obtained by the imaging with a reference format in which the attraction region and/or the avoidance region is set in advance.

According to this configuration, it is possible to determine an appropriate attraction region and/or avoidance region without manual operation.

A cancer evaluation method according to an eleventh aspect of the present invention, comprises:

the taxis analysis method according to any one of the first to the tenth aspect; and a step of evaluating a possibility of cancer in the subject using the taxis analysis result obtained by executing the taxis analysis.

According to this configuration, even if the container is imaged at any rotation angle from the position facing the bottom surface, the attraction region and the avoidance region can be correctly set on the basis of the position of the object of the reference point corresponding to the reference point, so that even if the container is imaged at any rotation angle from the position facing the bottom surface, it is possible to maintain accuracy of evaluation of taxis analysis.

A taxis analysis system according to a twelfth aspect of the present invention, the taxis analysis system for performing taxis analysis of nematodes using a container in which a reference point is provided in the container or a culture medium in the container, the taxis analysis system comprises:

a control unit configured to control an imaging unit to image a distribution mode of the nematodes in the container; and an analysis unit configured to detect a position of an object of the reference point included in an image obtained by the imaging and corresponding to the reference point, determine an attraction region and/or a avoidance region based on the position, and execute taxis analysis using objects of nematodes in the determined attraction region and/or avoidance region.

According to this configuration, the attraction region and the avoidance region can be correctly set with reference to the position of the object of the reference point corresponding to the reference point even if the container is imaged at any rotation angle from a position facing a bottom surface, so that it is possible to correctly perform taxis analysis of the nematodes even if the container is imaged at any rotation angle from the position facing the bottom surface.

A program according to a thirteenth aspect of the present invention, the program for performing taxis analysis of nematodes using a container in which a reference point is provided in the container or a culture medium in the container, the program causes a computer to be executed as:

an analysis unit configured to detect a position of an object of the reference point corresponding to the reference point included in an image obtained by imaging a distribution mode of the nematodes in the container, determine an attraction region and/or a avoidance region on a basis of the position, and execute taxis analysis using objects of nematodes in the determined attraction region and/or avoidance region.

According to this configuration, the attraction region and the avoidance region can be correctly set with reference to the position of the object of the reference point corresponding to the reference point even if the container is imaged at any rotation angle from a position facing a bottom surface, so that it is possible to correctly perform taxis analysis of the nematodes even if the container is imaged at any rotation angle from the position facing the bottom surface.

A taxis analysis method according to a fourteenth aspect of the present invention, the taxis analysis method for performing taxis analysis of nematodes, the taxis analysis method comprises steps of:

imaging a distribution mode of nematodes in the container; and executing taxis analysis using an area value of a region occupied by objects of nematodes in an attraction region and/or a avoidance region.

A cancer evaluation method according to a fifteenth aspect of the present invention, comprises:

the taxis analysis method according to the fourteenth aspect; and a step of evaluating a possibility of cancer in the subject by using a taxis analysis result obtained by executing the taxis analysis.

A taxis analysis system according to a sixteenth aspect of the present invention, the taxis analysis system for performing taxis analysis of nematodes, the taxis analysis system comprises:

a control unit configured to control an imaging unit to image a distribution mode of nematodes in a container after the nematodes and a specimen of a subject are dropped into the container; and an analysis unit configured to execute taxis analysis using an area value of a region occupied by objects of nematodes in an attraction region and/or a avoidance region.

A program according to a seventeenth aspect of the present invention, the program for performing taxis analysis of nematodes, the program causes a computer to be executed as:

an analysis unit configured to execute taxis analysis using an area value of a region occupied by objects of nematodes in an attraction region and/or a avoidance region included in an image obtained by imaging a distribution mode of nematodes in a container after the nematodes and a specimen of a subject are dropped into the container.

Advantageous Effects of Invention

According to one aspect of the present invention, an attraction region and a avoidance region can be correctly set with reference to a position of an object of a reference point corresponding to the reference point even if a container is imaged at any rotation angle from a position facing a bottom surface, so that taxis analysis of nematodes can be correctly performed even if the container is imaged at any rotation angle from the position facing the bottom surface.

BRIEF DESCRIPTION OF DRAWINGS

FIG. 6 is an example of a table of inspection information stored in a storage.

FIG. 23 is a flowchart illustrating an example of processing in step S460 in FIG. 22.

DESCRIPTION OF EMBODIMENTS

Figure 1:
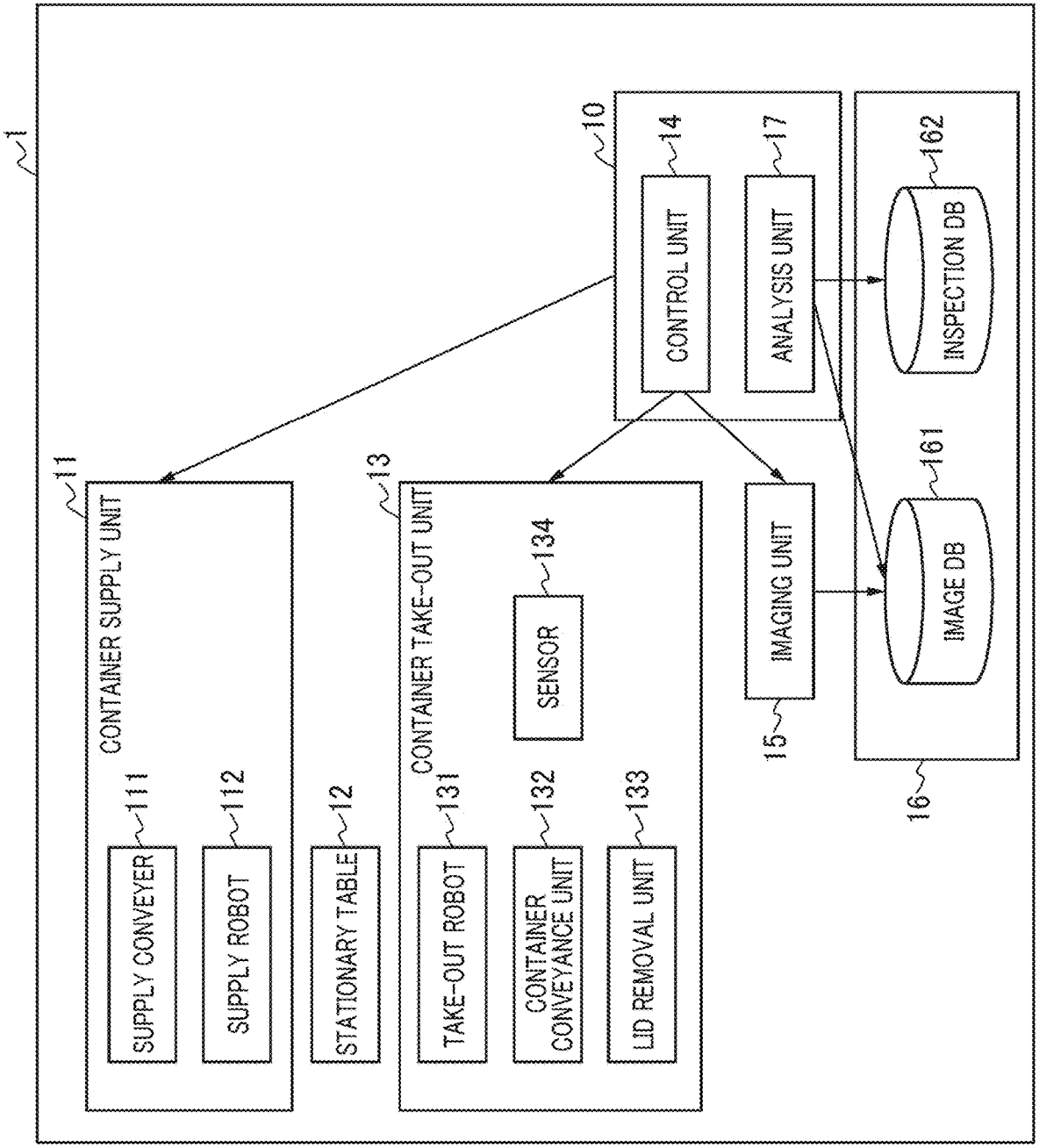
FIG. 1 is a block diagram illustrating a schematic configuration of a taxis analysis system according to the present embodiment.

Hereinafter, embodiments will be described with reference to the drawings. However, unnecessarily detailed description may be omitted. For example, detailed description of well-known matters and repeated description of substantially the same configuration may be omitted. This is to avoid unnecessary redundancy of the following description and to facilitate understanding of those skilled in the art.

In the present embodiment, "nematodes" mean *Caenorhabditis elegans*. The nematode is a popular organism that has been widely raised and studied in the world as a model organism in biological research and has characteristics of easy breeding and excellent olfactory sense.

In the present embodiment, "cancer" means a cancer type such as gastric cancer, colorectal cancer, esophageal cancer, pancreatic cancer, prostate cancer, bile duct cancer, lung cancer, blood cancer, leukemia, and lymphoma.

In the present embodiment, "taxis behavior" means attraction behavior or avoidance behavior. The attraction behavior means behavior of reducing a physical distance from a certain substance, and the avoidance behavior means behavior of increasing a physical distance from a certain substance. A substance that induces attraction behavior is referred to as an attractant, and a substance that induces avoidance behavior is referred to as a repellent. In addition, in the present embodiment, "taxis analysis" means analyzing taxis behavior.

In the present embodiment, a "reference point" refers to a mark (for example, printing, patterns, and the like) or a morphological change (for example, grooves, protrusions, and the like) provided on a container or a culture medium in order to recognize a rotation angle of a bottom surface of the container on a plane including the bottom surface. For example, in a case of a circular Petri dish, it is possible to distinguish between an attraction region and a avoidance region by providing a reference point having an asymmetric shape or providing a reference point having an arbitrary shape at a part other than a center point of the bottom surface.

As an example, a method and a system for taxis analysis according to the present embodiment are used to evaluate a possibility of cancer in a subject by using the taxis behavior of nematodes as an index. However, the taxis analysis method and the taxis analysis system according to the present embodiment can be used not only for nematodes but also for taxis analysis of other organisms and cells, and not only for evaluation of a possibility of cancer but also for evaluation of the possibility of other diseases.

The container according to the present embodiment is a container having a line-symmetric or point-symmetric shape on an inner bottom surface, and in the present embodiment, as an example, the container is a container having a point-symmetric shape, and specifically, will be described as a circular Petri dish. In addition, in the present embodiment, the description will be given on the assumption that the container or the culture medium in the container is provided with the reference point in a region other than the point symmetry point (here, the center of the Petri dish because the container is a circular Petri dish).

In a case where the container has a line-symmetric shape, the reference point is provided in a region other than the symmetry axis in the container or the culture medium in the container.

FIG. 1 is a block diagram illustrating a schematic configuration of a taxis analysis system according to the present embodiment. As illustrated in FIG. 1, a taxis analysis system 1 according to the present embodiment includes a processor 10, a container supply unit 11, a stationary table 12, a container take-out unit 13, an imaging unit 15, and a storage 16.

The container supply unit 11 is a unit that conveys the container after the nematodes and a specimen of a subject (for example, urine sample) are dropped, to the stationary table 12. After the nematodes and the specimen of the subject are dropped, a lid is put on the container, and the container is conveyed to the stationary table 12 in a state where the lid is put on the container. Here, the container supply unit 11 includes a supply conveyor 111 that conveys the container to a predetermined position, and a supply robot 112 that conveys the container from the predetermined position to the stationary table 12.

The stationary table 12 is a table for leaving the container in a stationary manner for a predetermined period, for example, at room temperature. During this predetermined period, the nematodes perform attraction behavior or avoidance behavior with respect to the specimen.

The container take-out unit 13 is a unit that takes out the container and conveys the container to a predetermined imaging position (for example, a focal position of the imaging unit 15). As an example, the container take-out unit 13 includes a take-out robot 131 that takes out the container from the stationary table 12, a container conveyance unit 132 that conveys the container to the predetermined imaging position, a lid removal unit 133 that removes the lid of the container, and a sensor 134.

The storage 16 stores a program to be read and executed by the processor 10. The processor 10 functions as a control unit 14 and an analysis unit 17 by reading and executing the program stored in the storage 16.

The control unit 14 controls the container supply unit 11, the container take-out unit 13, and the imaging unit 15.

The storage 16 also stores an image database (also referred to as an image DB) 161 and an inspection database (also referred to as an inspection DB) 162.

The imaging unit 15 images a distribution mode of the nematodes in the container conveyed by the container take-out unit 13 and stores an image obtained by the imaging in the image database 161 of the storage 16.

The analysis unit 17 reads the image from the image database 161 of the storage 16 and executes taxis analysis using the image obtained by imaging.

Then, the analysis unit 17 evaluates a possibility of cancer in the subject by using a taxis analysis result obtained by executing the taxis analysis. The analysis unit 17 stores the taxis analysis result and an evaluation result of the possibility of cancer in the subject (hereinafter, also referred to as a cancer evaluation result) in the inspection database 162 of the storage 16 as inspection information.

Figure 2:
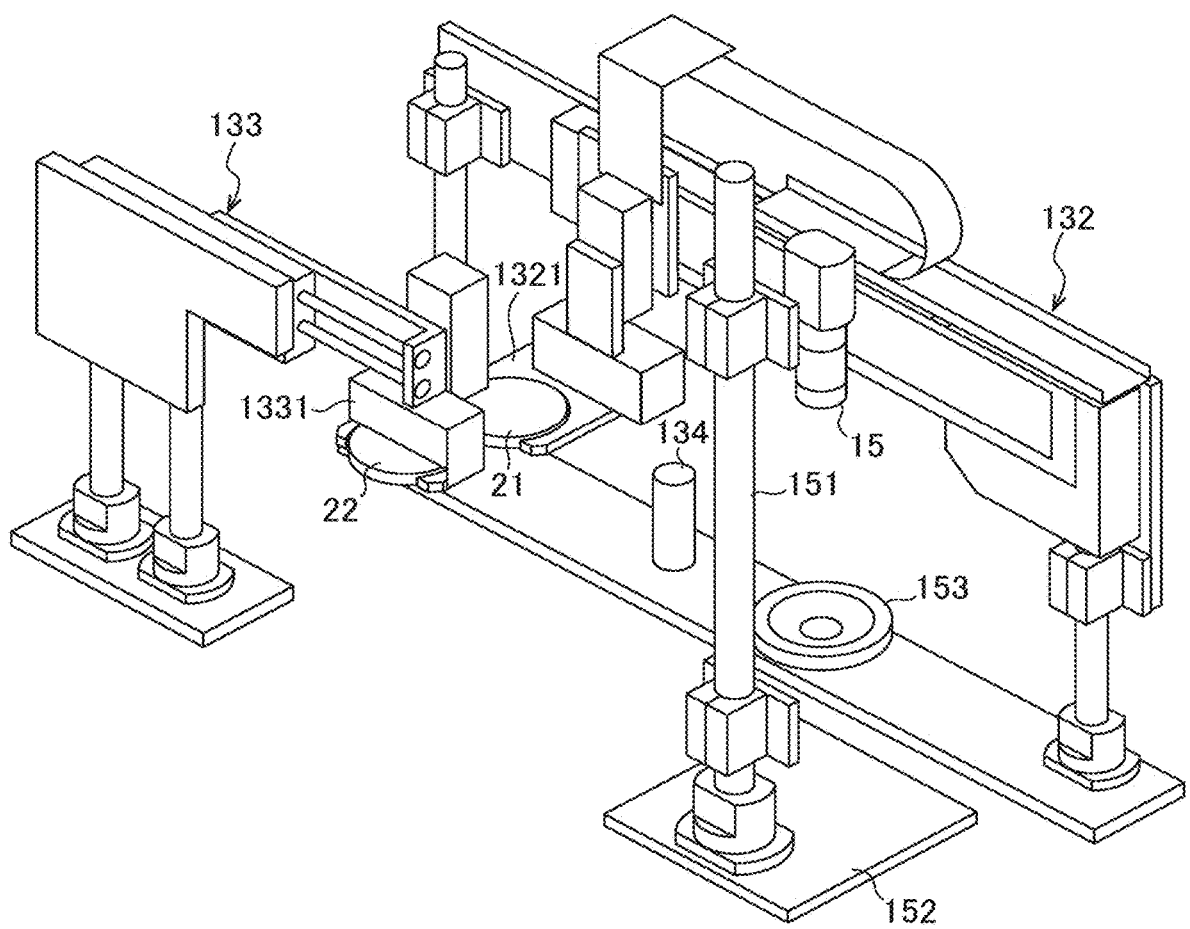
FIG. 2 is an example of a schematic perspective view of a container take-out unit 13 in a state before a container is conveyed.

FIG. 2 is an example of a schematic perspective view of the container take-out unit 13 in a state before the container is conveyed. In FIG. 2, the container conveyance unit 132 has a robot hand 1321 that grips a Petri dish 21 which is an example of the container. On the other hand, the lid removal unit 133 has an arm 1331 that grips a lid 22 of the Petri dish 21.

The sensor 134 detects whether or not the robot hand 1321 of the container conveyance unit 132 is located at a predetermined position and outputs a detection result to the control unit 14. In a case where the sensor 134 detects whether or not the robot hand 1321 is located at a predetermined position, the control unit 14 moves the arm 1331 of the lid removal unit 133 to the predetermined position and controls the arm 1331 to grip the lid 22 of the Petri dish 21.

As illustrated in FIG. 2, the imaging unit 15 is fixed to a support column 151, and the support column 151 is fixed on a base member 152. A light source 153 is fixed to the support column 151. The Petri dish 21 from which the lid 22 is removed is conveyed immediately below the imaging unit 15 by the container conveyance unit 132.

Figure 3:
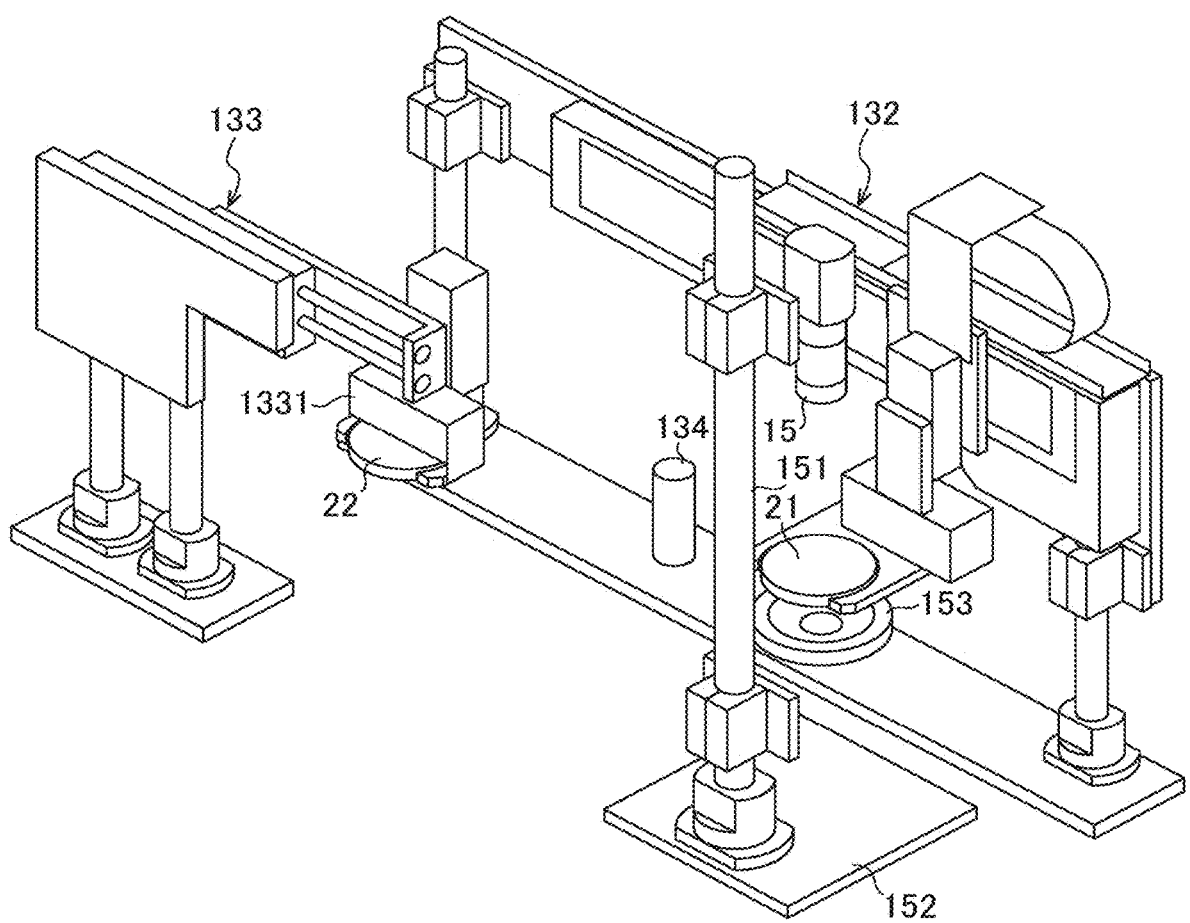
FIG. 3 is an example of a schematic perspective view of the container take-out unit 13 in a state after the container is conveyed.

FIG. 3 is an example of a schematic perspective view of the container take-out unit 13 in a state after the container is conveyed. As illustrated in FIG. 3, the Petri dish 21 from which the lid 22 is removed is moved immediately below the imaging unit 15 as an example. The position of the Petri dish 21 is preferably separated by a focal length of the imaging unit 15. In a state where the Petri dish 21 is illuminated with light from the bottom of the Petri dish 21 by a light source 153, a distribution mode of the nematodes in the Petri dish 21 is imaged by the imaging unit 15.

Figure 4:
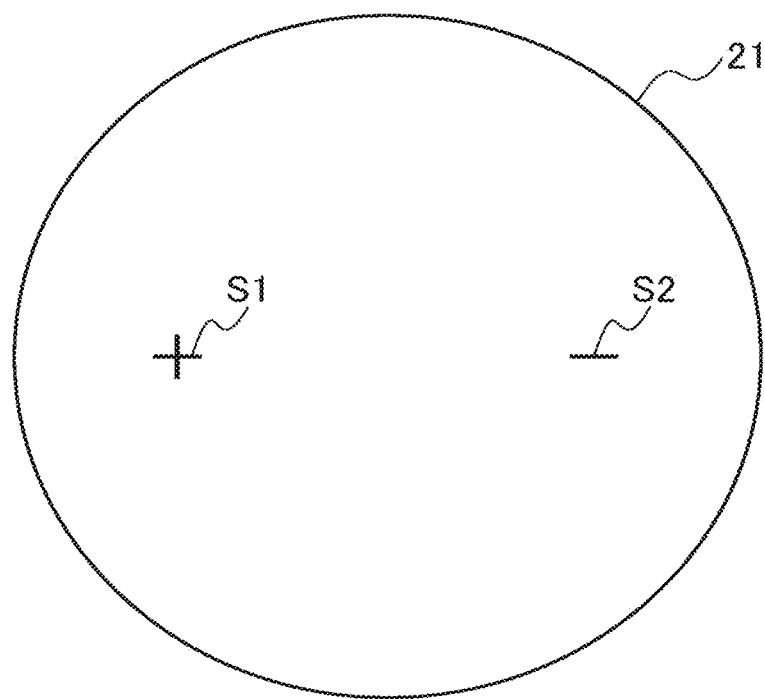
FIG. 4 is an example of a view of a Petri dish according to the present embodiment as viewed from above.

FIG. 4 is an example of a view of the Petri dish according to the present embodiment as viewed from above. As illustrated in FIG. 4, as an example, a reference point S1 indicating positive and a reference point S2 indicating negative are provided on the bottom surface of the Petri dish 21. In FIG. 4, as an example, the reference points S1 and S2 are provided at point-symmetrical positions with respect to the center of the Petri dish 21. In other words, the reference points S1 and S2 have the same distance from the center of the Petri dish 21, and the centers of the reference points S1 and S2 and the Petri dish 21 are on the same straight line. In addition, the reference points S1 and S2 may be printed on the Petri dish 21 or may be expressed by providing unevenness on the Petri dish 21. Note that a sheet on which the reference points S1 and S2 are printed may be attached to the bottom surface of the Petri dish using a printed surface as an attachment surface.

Note that the positions of the reference points S1 and S2 in the bottom surface of the Petri dish 21 are merely examples, and the positions are not limited thereto. In addition, the reference points S1 and S2 may be positioned on a side surface of the Petri dish 21 or may be provided in the culture medium.

Figure 5:
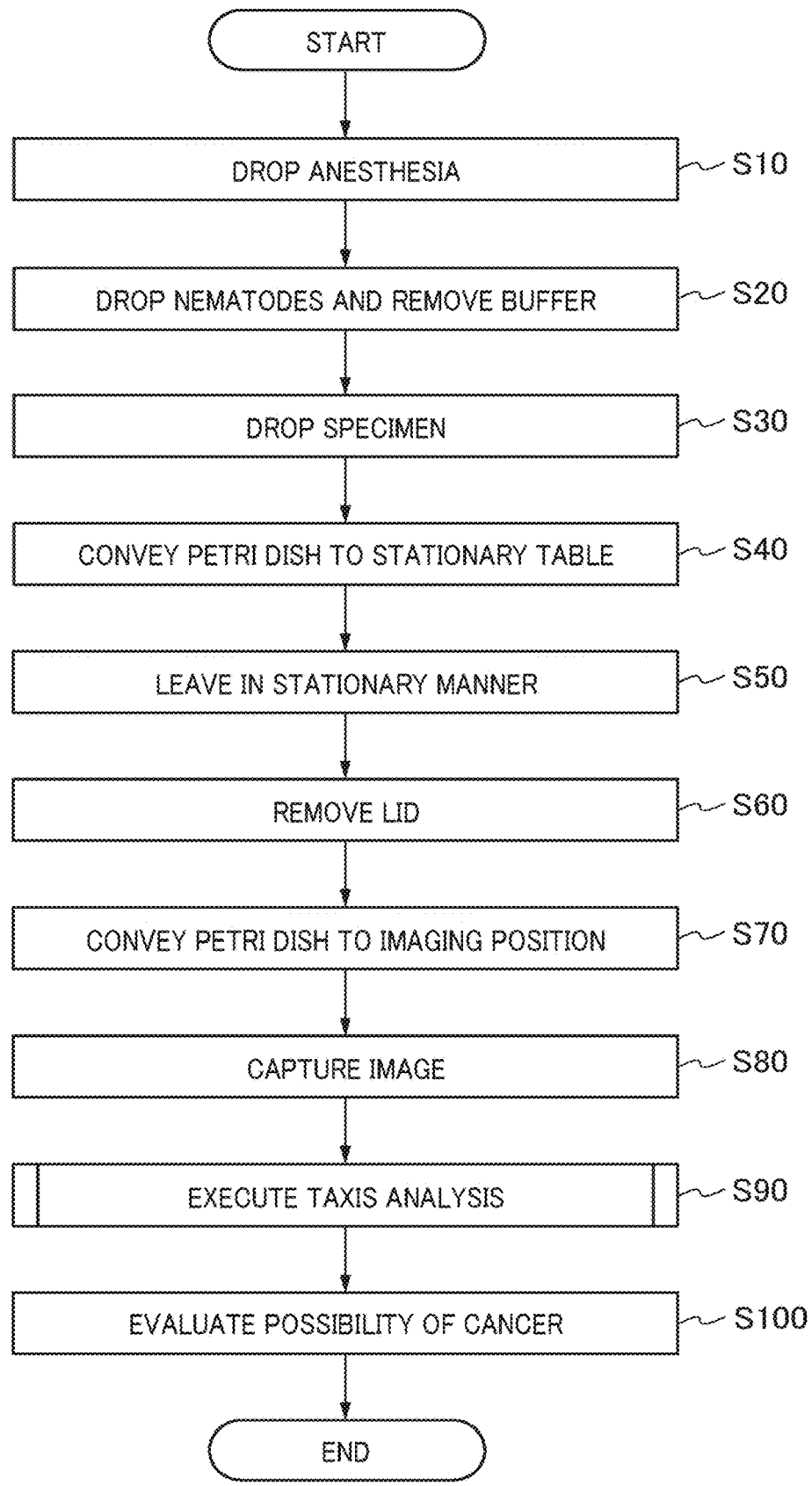
FIG. 5 is a flowchart illustrating an example of processing of taxis analysis according to the present embodiment.

FIG. 5 is a flowchart illustrating an example of processing of taxis analysis according to the present embodiment.

(Step S10) First, anesthesia is dropped onto a culture medium whose horizontal position corresponds to the positions of the reference point S1 and the reference point S2. As a result, when nematodes reach the position of the reference point S1 or the reference point S2 or the vicinity thereof, the nematodes cannot move due to anesthesia.

(Step S20) Next, nematodes are dropped onto the culture medium corresponding to the substantially central position of the Petri dish 21, and a buffer is removed with a nonwoven fabric, a dispenser, or the like.

(Step S30) Next, a urine sample derived from a cancer patient is dropped onto the culture medium whose horizontal position corresponds to the position of the reference point S1. As a result, when the nematodes are attracted by the smell of urine and reach the position of the reference point S1 or the vicinity thereof, the nematodes cannot move due to anesthesia.

Note that the order of steps S10 to S30 may be different.

(Step S40) Next, the container supply unit 11 conveys the Petri dish 21 to the stationary table 12.

(Step S50) Next, the Petri dish 21 is left in a stationary manner on the stationary table 12 for a predetermined period.

(Step S60) Next, the take-out robot 131 takes out the Petri dish 21 from the stationary table 12, and the lid removal unit 133 removes the lid 22 from the Petri dish 21. In this manner, before inside of the Petri dish 21 is imaged, the lid 22 of the Petri dish 21 is removed.

(Step S70) Next, the container conveyance unit 132 conveys the Petri dish 21 to a predetermined imaging position.

(Step S80) Next, the imaging unit 15 images a distribution mode of the nematodes in the Petri dish 21.

(Step S90) Next, the analysis unit 17 executes taxis analysis.

(Step S100) Next, the analysis unit 17 evaluates a possibility of cancer in the subject by using a taxis analysis result obtained by executing the taxis analysis. Then, the analysis unit 17 stores the taxis analysis result and an evaluation result of the possibility of cancer in the subject as inspection information in the inspection database 162 of the storage 16. As a result, the inspection information as illustrated in FIG. 6 is accumulated.

FIG. 6 is an example of a table of the inspection information stored in the storage. As illustrated in FIG. 6, a table T1 accumulates records of a set of a subject ID which is subject identification information for identifying a subject, a Petri dish ID which is an example of container identification information for identifying a container (here, a Petri dish as an example), a stationary start date and time, a stationary end date and time, a temperature during stationary, an imaging ID for identifying an image obtained by imaging, the number of attracted nematodes, the number of repelled nematodes, a taxis index, and a cancer evaluation result. Here, the taxis index is an example of a taxis analysis result, and the expression is, for example, the taxis index=(the number of nematodes exhibiting attraction behavior−the number of nematodes exhibiting avoidance behavior)/the total number of nematodes.

Figure 7:
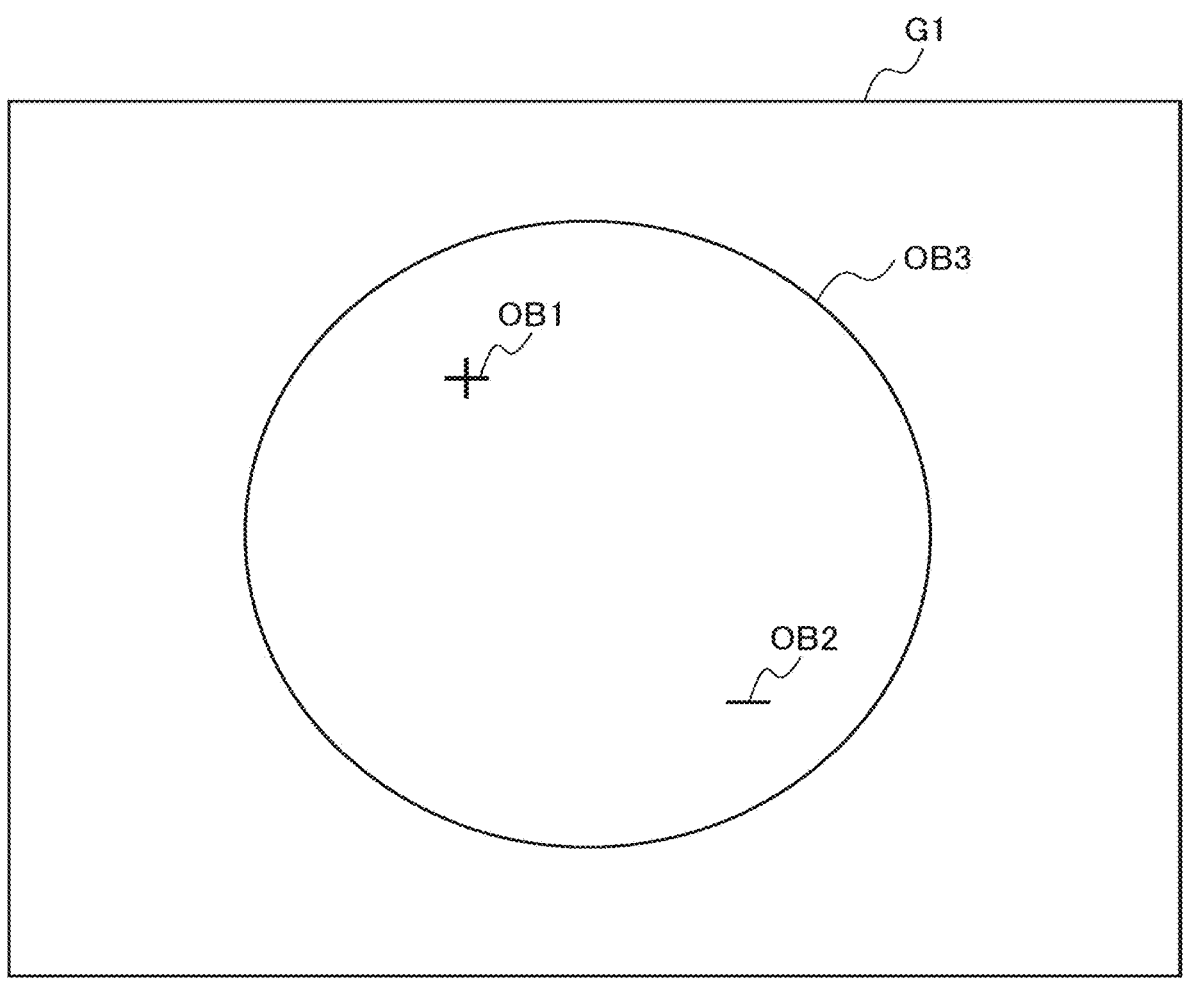
FIG. 7 is a schematic diagram of an image obtained by imaging according to the present embodiment.

FIG. 7 is a schematic diagram of an image obtained by imaging according to the present embodiment. As illustrated in FIG. 7, an object OB3 of the Petri dish 21, an object OB1 of the reference point S1, and an object OB2 of the reference point S2 are illustrated in the image obtained by imaging.

Figure 8:
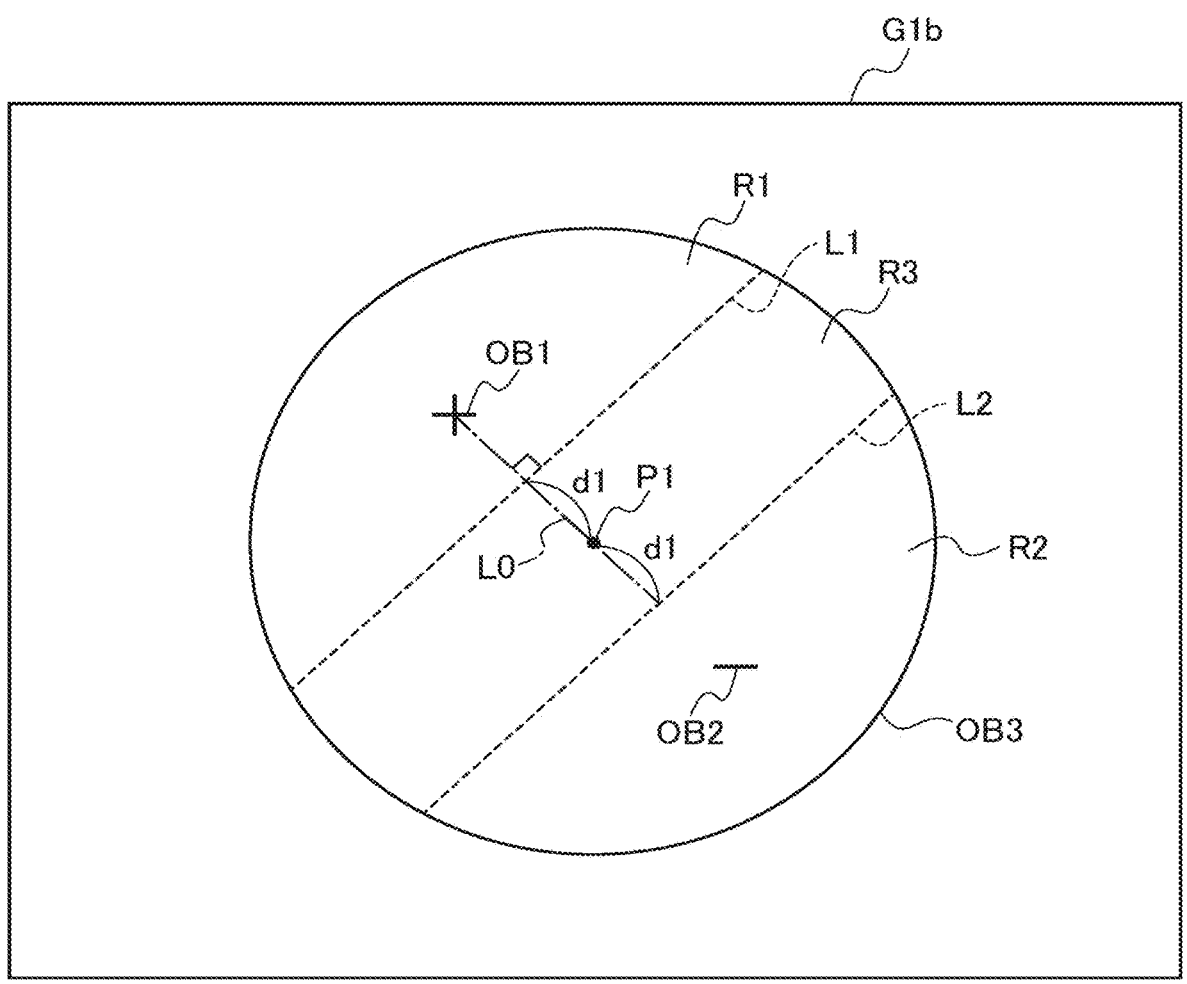
FIG. 8 is a schematic diagram illustrating an example of an attraction region and a avoidance region in the image obtained by imaging.

FIG. 8 is a schematic diagram illustrating an example of the attraction region and the avoidance region in an image obtained by imaging. As illustrated in FIG. 8, in an image obtained by imaging G1$b$, a center P1 of the object OB3 of the Petri dish 21 is extracted as a point at which two straight lines that are orthogonal to tangents of a contour of the object OB3 of the Petri dish 21 and that are drawn from two different positions on the contour, intersect each other. A straight line L1 orthogonal to the straight line L0 can be drawn at a position close to the object OB1 by a distance d1 from the center P1 along the straight line L0 connecting the center P1 of the object OB3 of the Petri dish 21 and the object OB1 of the reference point S1. In the straight line L0, a straight line L2 orthogonal to the straight line L0 can be drawn at a position away from the object OB1 by the distance d1 from the center P1. A region R1 surrounded by the straight line L1 and the contour of the object OB3 of the Petri dish 21 is an attraction region. A region R2 surrounded by the straight line L2 and the contour of the object OB3 of the Petri dish 21 is a avoidance region.

In a case of the example of FIG. 8, as a method of determining the attraction region, for example, the analysis unit 17 extracts the center P1 of the object OB3 of the Petri dish 21 from the image obtained by imaging G1$b$. Furthermore, the analysis unit 17 detects a position of the object OB1 at the reference point S1 from the image obtained by imaging G1$b$, for example. For example, the analysis unit 17 sets the straight line L1 orthogonal to the straight line L0 at a position close to the object OB1 by the distance d1 from the center P1 along the straight line L0 connecting the center P1 of the object OB3 of the Petri dish 21 and the object OB1 of the reference point S1 and determines the region R1 surrounded by the straight line L1 and the contour of the object OB3 of the Petri dish 21 as the attraction region. In addition, as a method of determining the avoidance region, in a case of the example of FIG. 8, the straight line L2 orthogonal to the straight line L0 is set at a position away from the object OB1 by the distance d1 from the center P1 along the straight line L0, and the region R2 surrounded by the straight line L2 and the contour of the object OB3 of the Petri dish 21 is determined as the avoidance region.

Note that the analysis unit 17 does not have to extract the center P1 of the object OB3 of the Petri dish 21 from the image obtained by imaging G1$b$. In a case where the reference point S1 and the reference point S2 are at point-symmetrical positions with respect to the center of the Petri dish 21, the analysis unit 17 may extract the object OB1 of the reference point S1 and the object OB2 of the reference point S2 from the image obtained by imaging G1$b$ and may set a straight line passing through the center of the object OB1 of the reference point S1 and the center of the object OB2 of the reference point S2 as the straight line L0.

As described above, the analysis unit 17 reads the image from the image database 161 of the storage 16, detects the position of an object of the reference point (for example, object OB1 at reference point S1 in FIGS. 7 and 8) corresponding to the reference point included in the image obtained by imaging and determines the attraction region (for example, the region R1 in FIG. 8) and the avoidance region (for example, the region R2 in FIG. 8) on the basis of the position. Then, the analysis unit 17 performs taxis analysis using the objects of the nematodes in the determined attraction region and avoidance region.

In this event, the analysis unit 17 determines the number of objects of the nematodes in the attraction region as the number of nematodes exhibiting the attraction behavior. In addition, the analysis unit 17 determines the number of objects of the nematodes in the avoidance region as the number of nematodes exhibiting the avoidance behavior.

Figure 9:
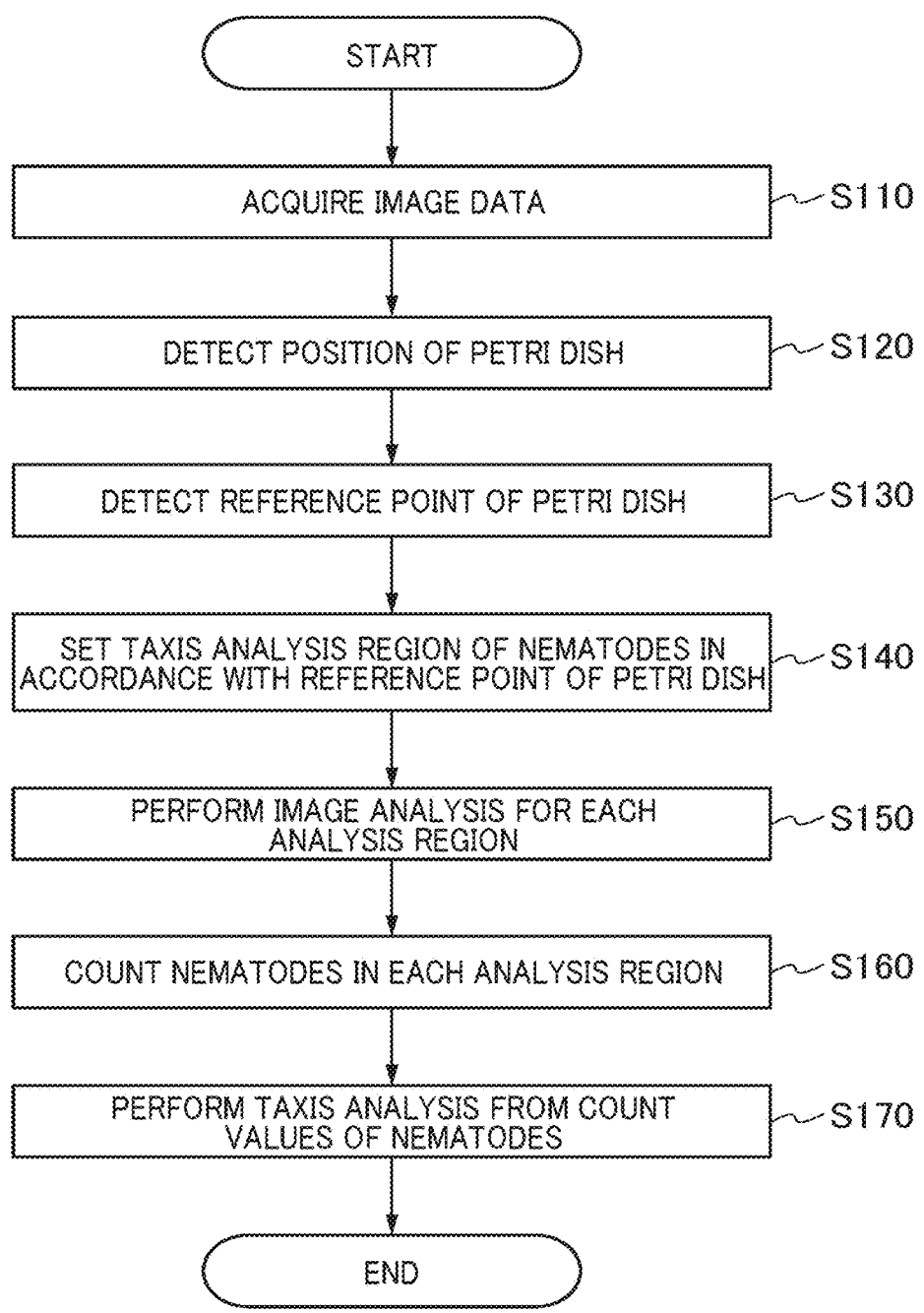
FIG. 9 is a flowchart illustrating an example of a taxis analysis method according to the present embodiment.

Next, a specific example of the taxis analysis processing in step S90 in FIG. 5 will be described with reference to FIG. 9. FIG. 9 is a flowchart illustrating an example of a taxis analysis method according to the present embodiment.

(Step S110) First, the analysis unit 17 of the processor 10 acquires image data from the image DB 161.

(Step S120) Next, the analysis unit 17 detects a position of the Petri dish in the image data.

(Step S130) Next, the analysis unit 17 detects a reference point of the Petri dish in the image data. For example, in a case where the image data is FIG. 8, the analysis unit 17 detects the object OB1 at the reference point S1 and/or the object OB2 at the reference point S2 from the image data G1b.

(Step S140) Next, the analysis unit 17 sets a nematode taxis analysis region in accordance with the reference point of the petri dish. In this event, for example, in a case where the image data is FIG. 8, the analysis unit 17 determines the region R1 in FIG. 8 as the attraction region and determines the region R2 in FIG. 8 as the avoidance region on the basis of the object OB1 at the reference point S1 and/or the object OB2 at the reference point S2.

(Step S150) Next, the analysis unit 17 performs image analysis for each analysis region determined in step S140. In this event, for example, the analysis unit 17 executes image processing for emphasizing contours of the nematodes in the image data.

(Step S160) Next, the analysis unit 17 counts the nematodes for each analysis region. In this event, for example, the analysis unit 17 counts regions of nematodes in the image data for each analysis region.

(Step S170) Next, the analysis unit 17 performs taxis analysis from the count value of the nematodes for each analysis region. In this event, for example, the analysis unit 17 calculates the taxis index. In this way, the nematodes in the determined attraction region are counted, the nematodes in the determined avoidance region are counted, and the taxis analysis result is output in accordance with the count results.

As described above, the taxis analysis method according to the present embodiment is a taxis analysis method for performing taxis analysis of nematodes using a container in which a reference point is provided in a region other than a symmetry axis or a region other than a symmetry point in the container or a culture medium in the container. This taxis analysis method includes steps of: imaging a distribution mode of the nematodes in the container after the nematodes and a specimen of the subject are dropped into the container; detecting a position of an object of the reference point corresponding to the reference point included in an image obtained by the imaging; determining an attraction region and a avoidance region on the basis of the position; and performing taxis analysis using objects of nematodes in the determined attraction region and avoidance region.

With this configuration, the attraction region and the avoidance region can be correctly set with reference to the position of the object of the reference point corresponding to the reference point even if the container is imaged at any rotation angle from the position facing the bottom surface, so that the taxis analysis of the nematodes can correctly be performed even if the container is imaged at any rotation angle from the position facing the bottom surface.

Note that step S130 can be omitted in FIG. 9. In this case, the container or the camera may be positioned such that the reference point of the container and the camera have a predetermined positional relationship at the imaging position in step S70 in FIG. 5. With this configuration, the orientation and the position of the container are always the same in the image obtained by imaging, which eliminates the need to correct the positions of the attraction region and the avoidance region from the image obtained by imaging, so that it is possible to correctly perform taxis analysis of the nematodes.

In addition, in the present embodiment, the analysis unit 17 evaluates a possibility of cancer in the subject by applying the taxis analysis result obtained by executing the taxis analysis to a predetermined evaluation rule. For example, in a case where the evaluation rule evaluates a possibility of cancer on the basis of whether or not the result is higher or lower than a threshold, the analysis unit 17 may evaluate that the possibility of cancer is high when the taxis analysis result is higher than the threshold and may evaluate that the possibility of cancer is low when the taxis analysis result is equal to or lower than the threshold. As a result, accuracy of evaluation of the possibility of cancer can be maintained regardless of the rotation angle at which the container is imaged from the position facing the bottom surface.

In the present embodiment, the positive and negative reference points are provided on the bottom surface of the Petri dish, but the present invention is not limited thereto, and the reference point may be provided on a side surface of the Petri dish, or the reference point may be provided on the culture medium.

MODIFICATION

Note that in the present embodiment, the positive and negative reference points are attached to the Petri dish, but the reference point is not limited thereto. The reference point may be a code (for example, a two-dimensional code) including container identification information for identifying the container.

Figure 10:
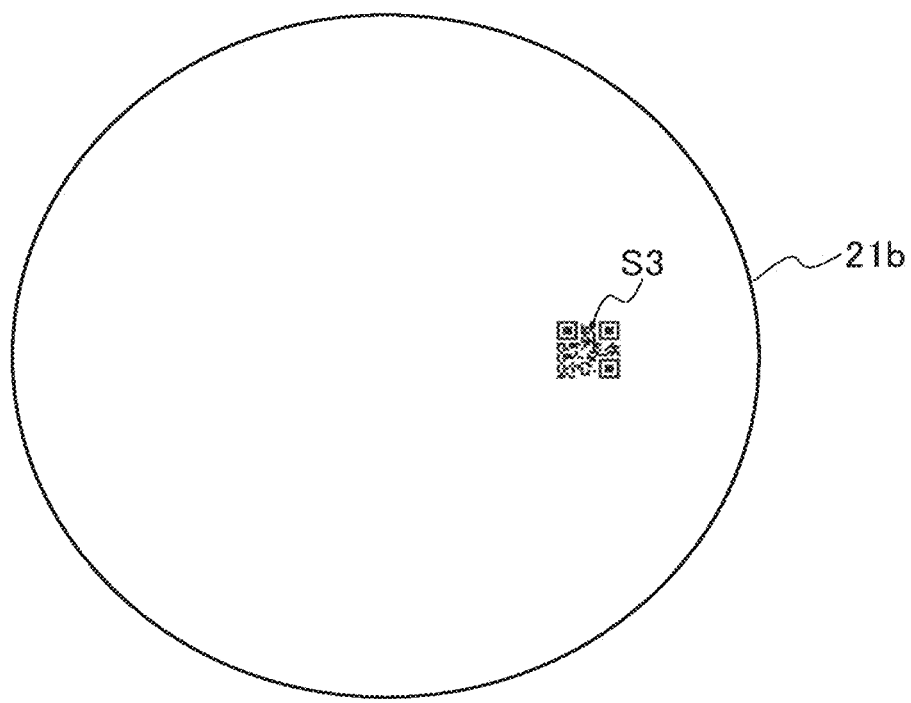
FIG. 10 is an example of a view of a Petri dish according to a modification as viewed from above.

FIG. 10 is an example of a view of a Petri dish according to a modification as viewed from above. As illustrated in FIG. 10, a two-dimensional code S3 is provided on a bottom surface of a Petri dish 21b. For example, the two-dimensional code may be printed on the Petri dish 21b or may be expressed by providing unevenness on the Petri dish 21b. Note that paper on which the two-dimensional code is printed may be attached to the bottom surface of the Petri dish 21b with a printing surface as an attachment surface.

Figure 11:
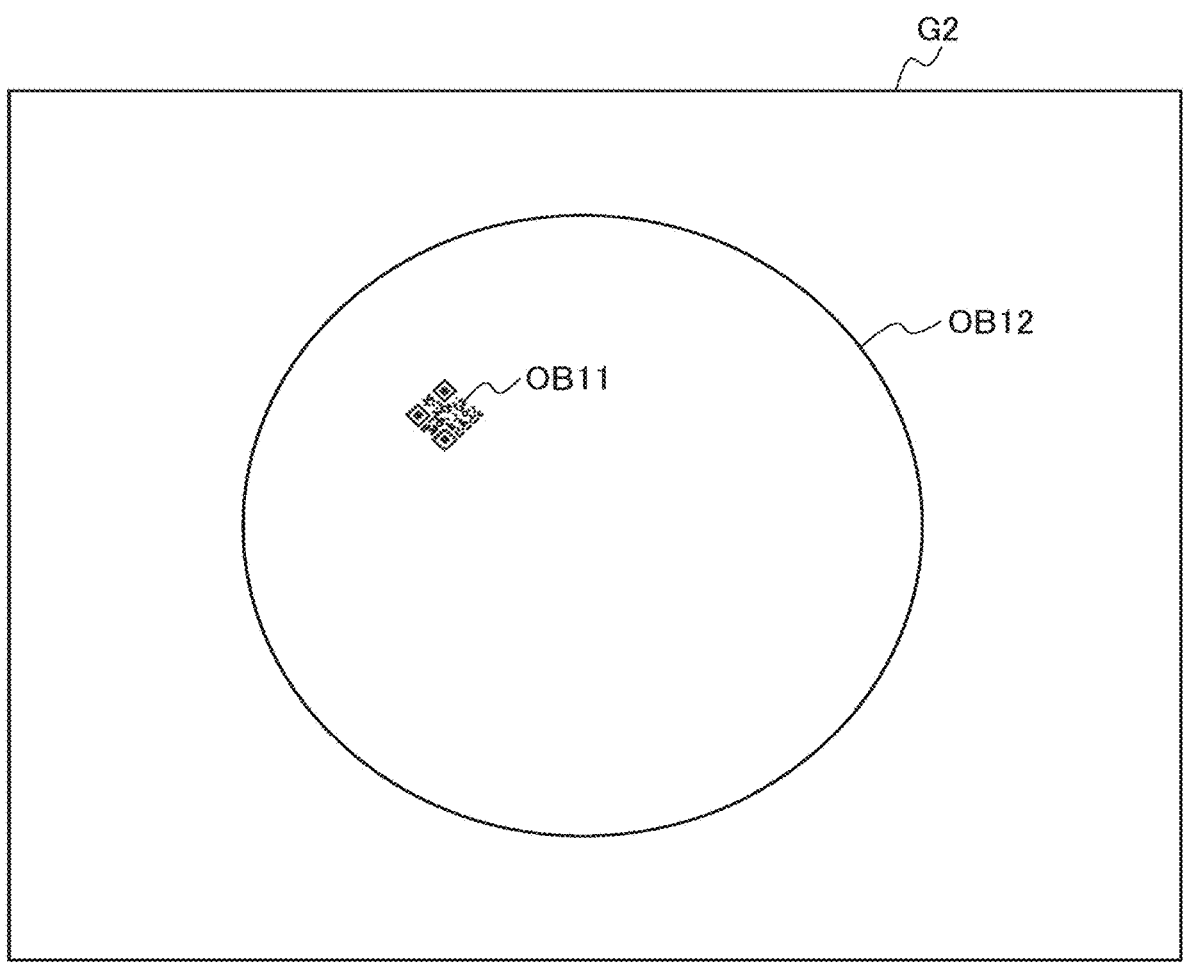
FIG. 11 is a schematic diagram of an image obtained by imaging according to the modification.

FIG. 11 is a schematic diagram of an image obtained by imaging according to the modification. As illustrated in FIG. 11, in an image obtained by imaging G2, a code object OB11 corresponding to the two-dimensional code S3 is included in an object OB12 corresponding to the Petri dish. As described above, the image obtained by imaging includes the code object corresponding to the code.

In this case, the analysis unit 17 reads the container identification information (here, the Petri dish ID as an example) from the code object OB11. Then, the analysis unit 17 stores a taxis analysis result which is a result of performing taxis analysis in the storage 16 in association with the read container identification information (here, Petri dish ID as an example).

With this configuration, the container identification information and the taxis analysis result can be managed in association with each other, and thus, if the subject identification information and the container identification information are managed in advance in association with each other, it is possible to specify the taxis analysis result of the subject and the taxis analysis result from the container identification information, so that it is possible to reduce the possibility of misidentifying a taxis analysis result of the subject.

When an urine specimen is dropped into a container (here, a Petri dish as an example), a combination of the subject of the urine specimen and the container is determined, and thus, in this event, subject identification information for identifying the subject and the container identification information may be stored in the storage 16 in association with each other to manage the subject and the container identification information in association with each other. In this case, the analysis unit 17 may specify the subject identification information corresponding to the container identification information read from the code object with reference to the storage 16. With this configuration, the subject can be specified from the container identification information, so that it is possible to reduce the possibility of misidentifying the taxis analysis result of the subject.

Similarly, the analysis unit 17 may output a set of subject identification information and a taxis analysis result or a set of subject identification information and a cancer evaluation result corresponding to the container identification information read from the code object with reference to the storage 16. With this configuration, the taxis analysis result or the cancer evaluation result for each subject can be obtained, so that it is possible to reduce the possibility of misidentifying the taxis analysis result or the cancer evaluation result of the subject.

As described above, the taxis analysis system according to the present embodiment is a taxis analysis system that performs taxis analysis of nematodes using the container or the container in which the reference point is provided in the culture medium. A taxis analysis system according to the present embodiment includes: a control unit configured to control an imaging unit to image a distribution mode of nematodes in a container after the nematodes and a specimen of a subject are dropped into the container; and an analysis unit configured to detect a position of an object of the reference point corresponding to the reference point included in the image obtained by the imaging, determine an attraction region and a avoidance region on the basis of the position, and execute taxis analysis using objects of the nematodes in the determined attraction region and avoidance region.

With this configuration, the attraction region and the avoidance region can be correctly set with reference to the position of the object of the reference point corresponding to the reference point even if the container is imaged at any rotation angle from the position facing the bottom surface, so that the taxis analysis of the nematodes can correctly be performed even if the container is imaged at any rotation angle from the position facing the bottom surface.

Figure 12:
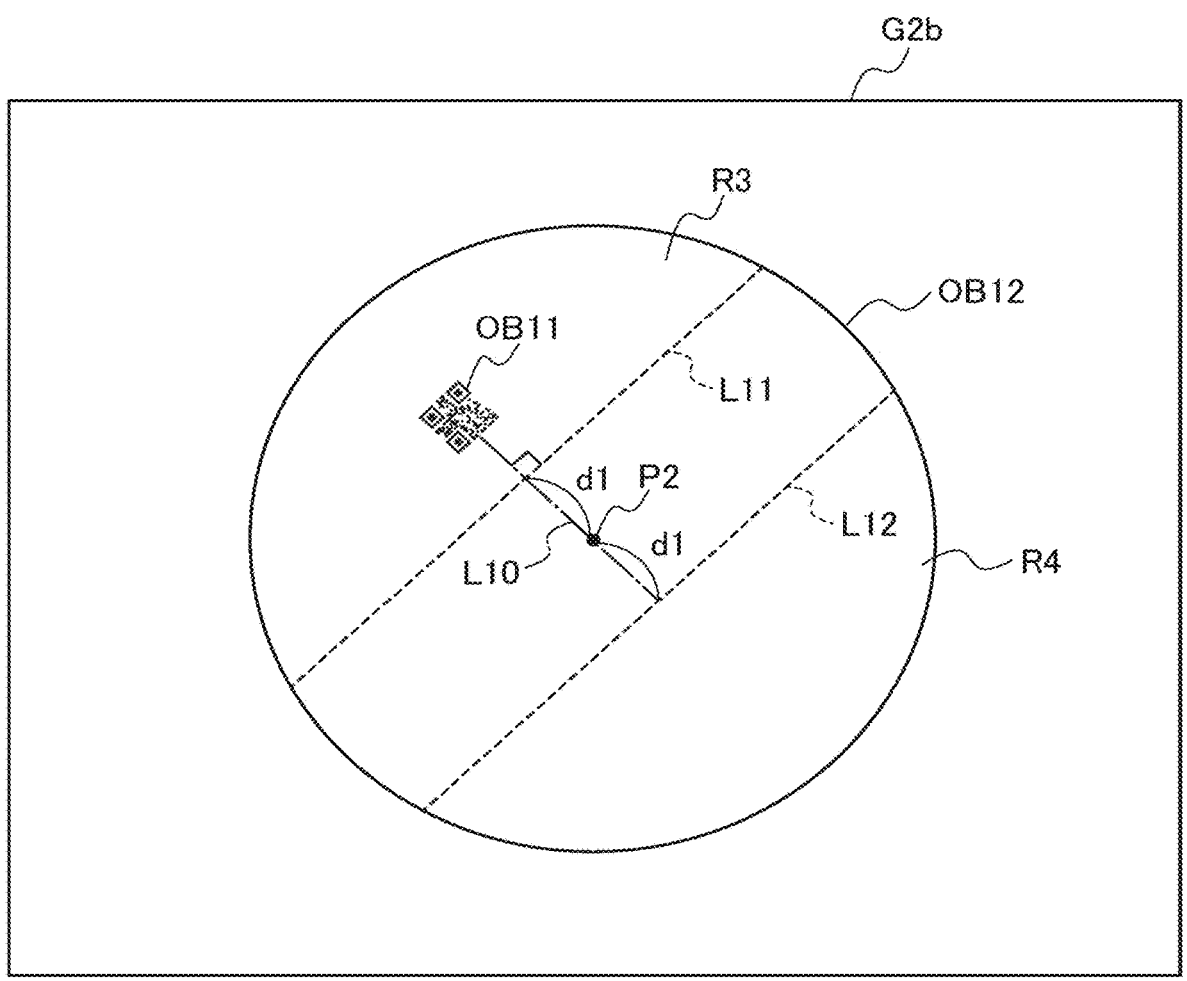
FIG. 12 is a schematic diagram illustrating an example of an attraction region and a avoidance region in the image obtained by imaging in the modification.

FIG. 12 is a schematic diagram illustrating an example of the attraction region and the avoidance region in the image obtained by imaging in the modification. As illustrated in FIG. 12, in a straight line L10 connecting the center P2 of the object OB12 of the Petri dish 21 and the code object OB11 of the two-dimensional code, a straight line L11 orthogonal to the straight line L10 can be drawn at a position close to the code object OB11 by a distance d1 from the center P2. Furthermore, in the straight line L10, a straight line L12 orthogonal to the straight line L10 can be drawn at a position away from the code object OB11 by the distance d1 from the center P2. A region R3 surrounded by the straight line L11 and the contour of the object OB12 of the Petri dish 21 is an attraction region. A region R4 surrounded by the straight line L12 and the contour of the object OB12 of the Petri dish 21 is a avoidance region.

In this case, the analysis unit 17 may read the image from the image database 161 of the storage 16, detect the position of the code object (for example, the code object OB11 of FIG. 12) corresponding to the two-dimensional code included in the image obtained by imaging, determine the attraction region (for example, the region R3 in FIG. 12) and the avoidance region (for example, the region R4 in FIG. 12) on the basis of the position and execute taxis analysis using objects of the nematodes in the determined attraction region and avoidance region. Note that the code is not limited to the two-dimensional code and may be a barcode.

Figure 13:
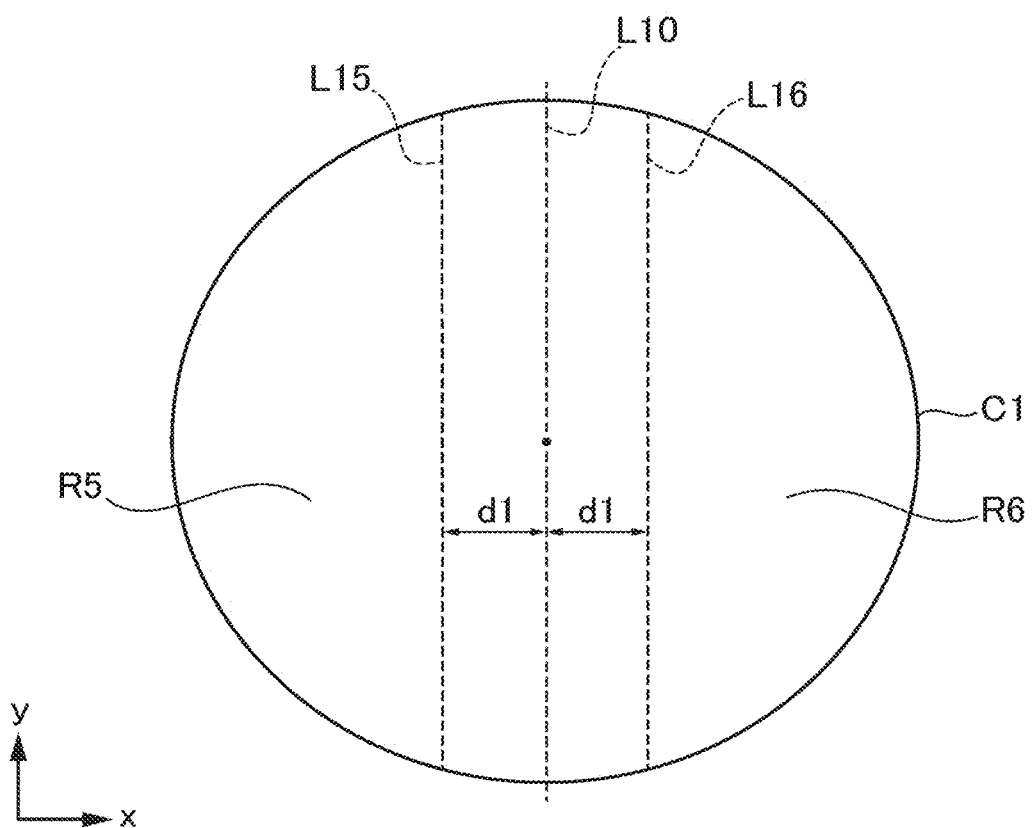
FIG. 13 is an example of a reference format stored in advance in a storage 16.

FIG. 13 is an example of a reference format stored in advance in the storage 16. As illustrated in FIG. 13, the reference format is a format serving as a reference for setting the attraction region and the avoidance region. In the reference format in FIG. 13, the straight line L10 passing through the center of the circle C1 and separated in parallel by a distance d in a −x direction with respect to a straight line L15 that is parallel to a y axis is illustrated. A region R5 defined by the straight line L15 and the circle C1 is a reference attraction region. Similarly, in the reference format in FIG. 13, the straight line L10 passing through the center of the circle C1 and separated in parallel in a +x direction by a distance d with respect to a straight line L16 that is parallel to the y axis is illustrated. A region R6 defined by the straight line L16 and the circle C1 is a reference avoidance region.

Figure 14:
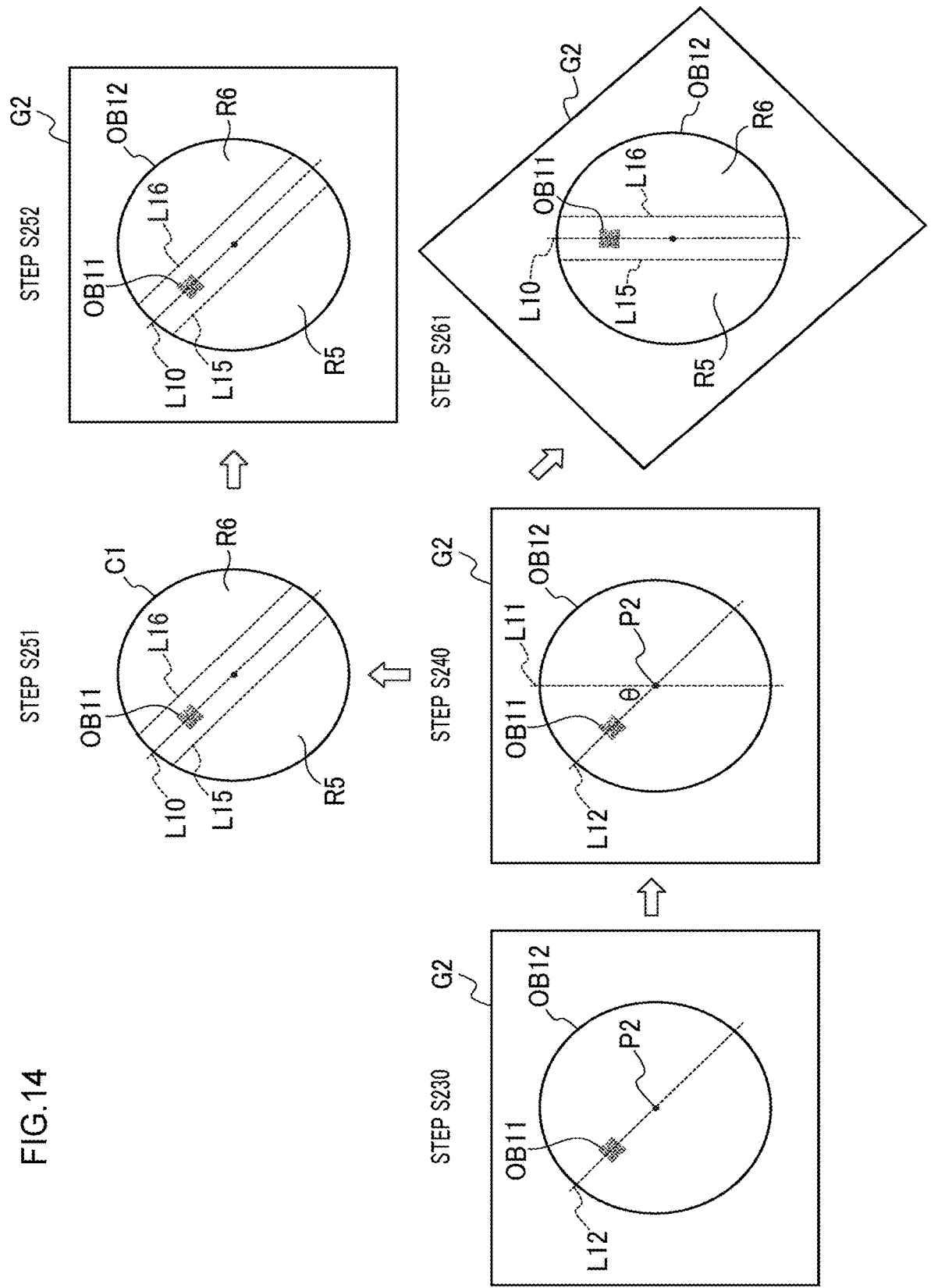
FIG. 14 is a schematic diagram illustrating an example of the attraction region and the avoidance region in the image obtained by imaging in the modification.

An example of processing in step S140 in FIG. 9 will be described with reference to FIG. 14. FIG. 14 is a schematic diagram illustrating an example of the attraction region and the avoidance region in the image obtained by imaging in the modification. The analysis unit 17 recognizes the Petri dish object OB12 by image processing and recognizes the center P2 of the Petri dish object OB12. Next, the analysis unit 17 recognizes a two-dimensional code, which is an example of the reference point, by image processing. Note that the order of the recognition processing of the center P2 and the recognition processing of the two-dimensional code may be reversed.

(Step S230) Next, the analysis unit 17 determines a straight line L12 (straight line L12 illustrated in FIG. 14) connecting the center P2 and the two-dimensional code.

(Step S240) Next, the analysis unit 17 obtains an angle θ (angle θ illustrated in FIG. 14) formed by the straight line L11 and the straight line L12 parallel to a longitudinal direction of the image G2 which is an example of the reference line.

Next, steps S251 and S252 are executed, or step S261 is executed.

(Step S251) As illustrated in FIG. 14, the analysis unit 17 rotates the reference format of FIG. 13 counterclockwise by θ about the center of the circle.

(Step S252) Next, as illustrated in FIG. 14, the analysis unit 17 superimposes the reference format after counterclockwise rotation by θ so that the center of the circle C1 of the reference format after counterclockwise rotation θ overlaps the center P2 of the Petri dish object OB12 in the image G2 or a case where the reference format is superimposed is assumed. Then, the analysis unit 17 sets the region R5 of the reference format after superimposition (or in a case where it is assumed that the reference format is superimposed) as the attraction region and sets the region R6 of the reference format after superimposition (or in a case where the reference format is superimposed) as the avoidance region.

Note that, at the time of superimposition, in a case where the circle C1 in the reference format does not match an outer periphery (that is, the contour) of the Petri dish object OB12 in the image G2, the analysis unit 17 may enlarge or reduce the circle C1 in the reference format so that the circle C1 in the reference format matches the outer periphery of the Petri dish object OB12 in the image G2. In this case, the analysis unit 17 sets a region R5 of the enlarged or reduced reference format as the attraction region and sets a region R6 of the enlarged or reduced reference format as the avoidance region.

(Step S261) The analysis unit 17 rotates the image G2 clockwise by θ. Next, the analysis unit 17 sets the region R5 between the straight line L15 parallel to the straight line L10 separated from the straight line L10 by the distance d1 and the contour of the object OB12 as the attraction region and sets the region R6 between the straight line L16 parallel to the straight line L10 separated from the straight line L10 by the distance d1 and the contour of the object OB12 as the avoidance region.

Note that, in step S261, the image G2 is rotated clockwise by θ, but the present invention is not limited thereto, and the robot hand 1321 may include a mechanism for holding and rotating the Petri dish, and the robot hand 1321 may physically rotate the Petri dish itself clockwise by θ while holding the Petri dish. In this case, the attraction region and/or the avoidance region may be determined by imaging the distribution mode of the nematodes in the container after the rotation and comparing an image obtained by the imaging with the reference format in which the attraction region and/or the avoidance region is set in advance. Note that, here, a modification in which the robot hand 1321 grips and rotates the Petri dish has been described, but the present invention is not limited thereto, and the Petri dish may be placed on a table (for example, a mortar base) provided with a recess on a surface and may be physically rotated by the robot hand 1321 in a state where the Petri dish is placed.

In the present embodiment, both the attraction region and the avoidance region are set, the number of nematodes in both regions is counted, and the taxis analysis is performed using the number of nematodes in both regions, but the invention is not limited thereto. The distribution of nematodes after left in a stationary manner tends to concentrate at a location where anesthesia is dropped to the culture medium. Thus, only one of the attraction region and the avoidance region may be set, the number of nematodes in the set region may be counted, and taxis analysis may be performed using the number of nematodes in the set region and the number of nematodes in the region of the Petri dish object OB12. For example, in a case where the attraction region is set, the number of nematodes in the avoidance region can be regarded as a value obtained by subtracting the number of nematodes in the attraction region from the number of nematodes in the region of the Petri dish object OB12 corresponding to an inner bottom surface of the Petri dish.

Note that in the present embodiment, the taxis analysis method illustrated in FIG. 9 is performed in order to evaluate the possibility of cancer in the subject, but the taxis analysis method is not limited to cancer evaluation and may be performed in a case where taxis of other organisms or cells is evaluated.

Second Embodiment

Next, a second embodiment will be described. A taxis index in related art is obtained by counting the number of nematodes by visual observation under a microscope. Specifically, the taxis action of nematodes has been evaluated using a taxis analysis value as an index, and a taxis index calculated from the following expression has been used.

$$\text{Taxis index} = (x-y)/(x+y)$$

Here, x is the number of nematodes that have exhibited attraction behavior with respect to the sample, and y is the number of nematodes that have exhibited avoidance behavior with respect to the sample, and this taxis index is the same as that of the first embodiment.

As a method of automatically calculating this taxis index, the following calculation method can be considered. In other words, when a camera is disposed from above the Petri dish on which the nematodes are placed and the Petri dish is irradiated by a light source from below the Petri dish, imaging is performed at higher luminance than the surroundings due to diffuse reflection of light generated by the nematodes, so that the region of the nematodes is identified. Then, there is a method in which calculation is performed by the following method using the image or moving image obtained by imaging.

(1) A method in which a taxis index is calculated by measuring a center of gravity of luminance of a predetermined region in the image obtained by imaging.

(2) A method in which the number of nematode regions is counted in a predetermined region in the image obtained by imaging.

In the case of (1) and (2), the number of regions having higher luminance than the surroundings is counted as the number of nematodes. However, if a plurality of nematodes are imaged in an overlapping state, the nematodes are recognized as one region, and the actual number of nematodes may be greatly different from the number of regions. For this reason, in a case where a computer automatically counts nematodes from an image, in a case where nematodes overlap in the image, it is difficult to accurately count the number of nematodes from the image, and there is a problem that the taxis index calculated by the computer is greatly different from the taxis index calculated by visually counting the nematodes by a human (hereinafter, referred to as a taxis index calculated by manual counting).

In addition, if a fixed threshold is set for regions to be counted, there is also a problem that accuracy of the taxis analysis value may decrease due to a difference in imaging conditions.

On the other hand, in the present embodiment, a method for determining a new taxis analysis value has been developed in order to automatically determine whether or not there is cancer from the image obtained by imaging the nematodes by a computer. In the present embodiment, the computer calculates the taxis index using the method for calculating a new taxis analysis value and automatically evaluates a possibility of cancer in the subject using the new taxis analysis value.

According to this, even in a case where the nematodes overlap in the image, the taxis analysis value calculated by the method for calculating the new taxis analysis value becomes a value close to "the taxis index calculated by manual counting", so that the computer can automatically determine a possibility of cancer in the subject from the image with accuracy equivalent to "the taxis index calculated by manual counting".

In addition, although an area of the objects corresponding to the nematodes relatively changes depending on the imaging conditions, according to the method for calculating a taxis analysis value according to the present embodiment, even if the imaging conditions change, a result is obtained in which a difference between the taxis analysis value calculated by the method for calculating the new taxis analysis value and the taxis index calculated by manually counting is small. Thus, in the present embodiment, the computer can automatically determine a possibility of cancer in the subject from the image with accuracy equivalent to that of "the taxis index calculated by manually counting" without being greatly affected by the imaging conditions.

<System Configuration>

Figure 15:
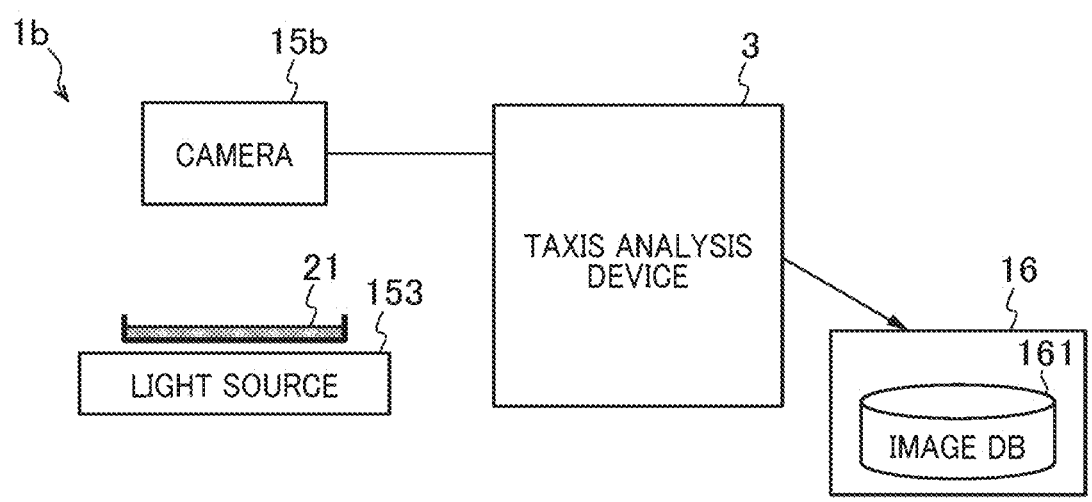
FIG. 15 is a schematic configuration diagram of a taxis analysis system according to a second embodiment.

FIG. 15 is a schematic configuration diagram of a taxis analysis system according to the second embodiment. A taxis analysis system 1b includes a light source 21, a camera 15b which is an example of an imaging unit, a taxis analysis device 3 which is connected to the camera 15b and a storage 16 which stores an image database (image DB) 161. The imaging unit 15 is disposed above the Petri dish 21 while light of the light source 21 is radiated from below the Petri dish 21 after the taxis test, and the taxis analysis device 3 images the Petri dish 21 to calculate a taxis analysis value. The light source 21 is desirably a circular white LED. The camera 15b is controlled by the taxis analysis device 3, and the image obtained by imaging by the camera 15b is accumulated in the image database 161.

Figure 16:
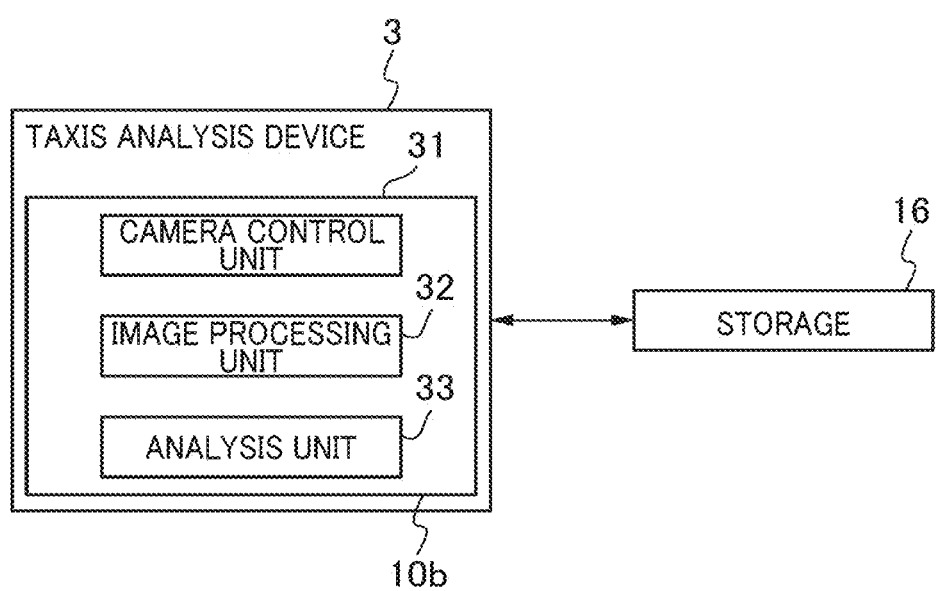
FIG. 16 is a block diagram of a taxis analysis device according to the second embodiment.

FIG. 16 is a block diagram of the taxis analysis device according to the second embodiment. As illustrated in FIG. 16, the taxis analysis device 3 according to the second embodiment includes a processor 10b, and the processor 10b functions as a camera control unit 31, an image processing unit 32, and an analysis unit 33 by reading and executing a program stored in the storage 16. The camera control unit 31 controls the camera 15b to image the Petri dish 21 and stores an image obtained by imaging in the image database 161 of the storage 16. The image processing unit 32 performs image processing. The analysis unit 33 calculates a taxis analysis value using the image after the image processing and evaluates a possibility of cancer using the taxis analysis value.

<Objects of Nematodes and Area Value>

Figure 17:
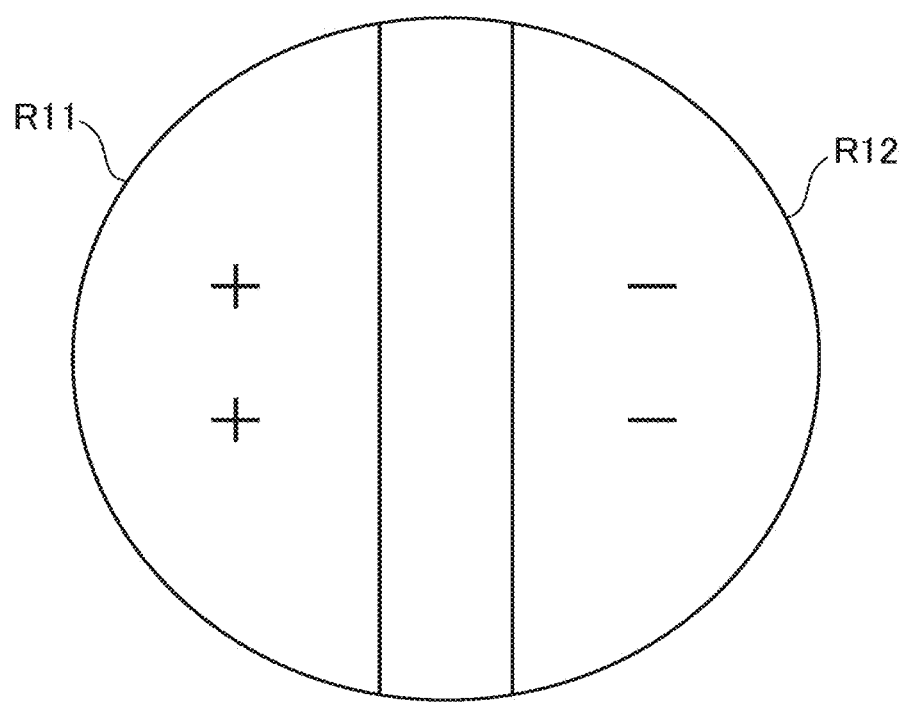
FIG. 17 is a schematic view of an image of a Petri dish on which taxis analysis is to be performed.
Figure 18:
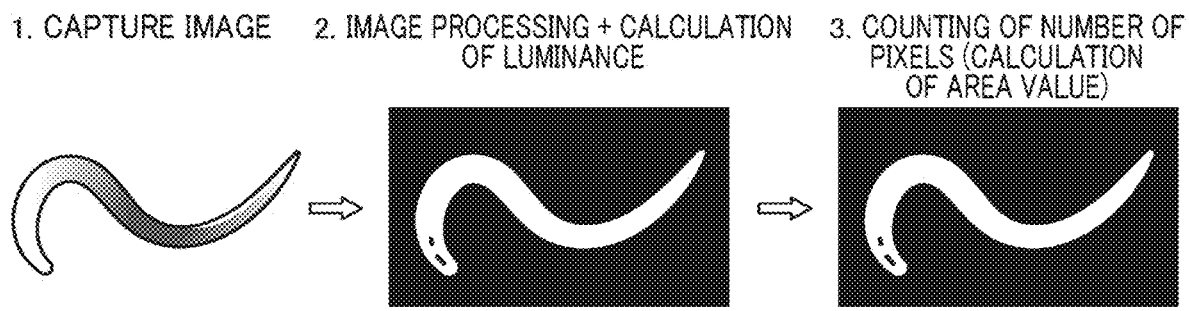
FIG. 18 is a view illustrating processes of processing according to the second embodiment.

FIG. 17 is a schematic view of an image of the Petri dish on which taxis analysis is to be performed. As illustrated in FIG. 17, an attraction region R11 in which it is determined that the nematodes exhibit the attraction behavior and a avoidance region R12 in which it is determined that the nematodes exhibit the avoidance behavior are illustrated. FIG. 18 is a diagram illustrating processes of processing according to the second embodiment. Hereinafter, the processes of the processing will be described with reference to FIG. 18.

The image processing unit 32 extracts regions occupied by objects of nematodes corresponding to the respective nematodes in each of the attraction region (also referred to as a positive region) and the avoidance region (also referred to as a negative region) illustrated in FIG. 17 by image processing (for example, edge extraction by hue, binarization processing, or the like) from the image obtained by imaging. Then, the analysis unit 33 calculates an area of the extracted objects of nematodes.

Specifically, for example, the analysis unit 33 counts the number of pixels occupied by the objects of nematodes.

There are two types of methods for calculating the taxis analysis value of the present embodiment, and in both methods, the taxis analysis value is calculated using the area value of the objects of nematodes. Each will be described below.

<First Calculation Method>

First, a first calculation method of the taxis analysis value of the present embodiment will be described. The first calculation method is a method in which the taxis analysis value is calculated using a sum of area values of objects of nematodes in the attraction region and a sum of area values of objects of nematodes in the avoidance region.

Figure 19:
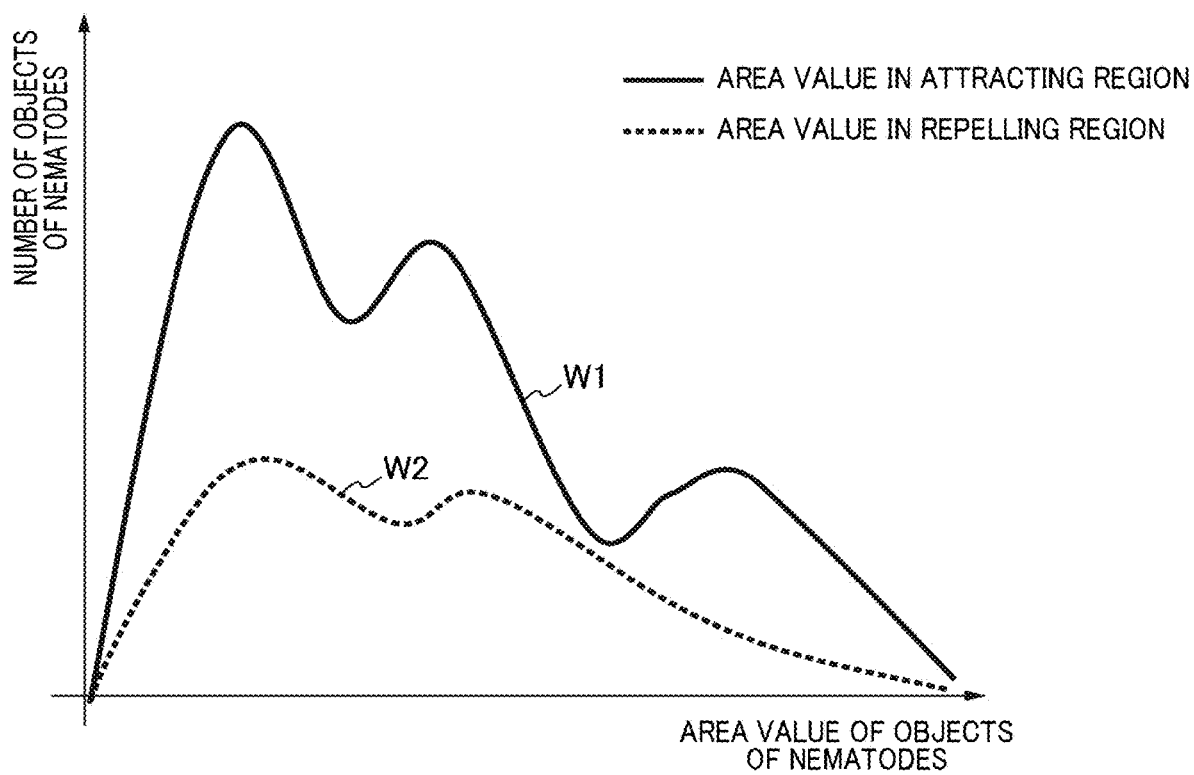
FIG. 19 is an example of a histogram of area values of objects of nematodes in the attraction region and the avoidance region.

FIG. 19 is an example of a histogram of area values of the objects of nematodes in the attraction region and the avoidance region. In the taxis test, adult worms having substantially the same size are used as the nematodes, but the area value of an object of each nematode varies due to light diffusely reflected by the nematodes at the time of imaging. (1) Regarding this variation, it is observed that variations in area values of the attraction region and the avoidance region are substantially the same. From this, even if the taxis analysis value was calculated using the following expression, the taxis analysis value was less different from the taxis index calculated by manual counting.

$$I=(S_A-S_B)/(S_A+S_B) \qquad (1)$$

Here, I is the taxis analysis value, $S_A$ is a sum of the area values of the objects of nematodes in the attraction region, and $S_B$ is a sum of the area values of the objects of the nematodes in the avoidance region. The above expression (1) is used to calculate the taxis analysis value in the flowchart of FIG. 20 which will be described later. Note that only one of the attraction region and the avoidance region may be set, and the area value of the objects of the nematodes in the set region and the area value of the objects of the nematodes in the entire region of the Petri dish object OB12 may be used to perform taxis analysis. For example, in a case where the attraction region is set, the area value of the objects of the nematodes in the avoidance region can be regarded as a value obtained by subtracting the area value of the objects of the nematodes in the attraction region from the area value of the objects of the nematodes in the entire region of the Petri dish object OB12 corresponding to the inner bottom surface of the Petri dish.

In addition, (1) no deviation in chemotaxis action depending on the size of the adult nematodes used for the test is observed even when there are individual differences in the size of the adult nematodes, (2) in most tests, in distribution of the nematodes after the test, a state where one nematode is in a stationary state is more often seen than a state where a plurality of nematodes overlap each other, (3) even if a result of a small absolute value of the taxis analysis value is obtained in a cancer test, states where a plurality of nematodes overlap each other tend not to be unevenly distributed in each of the attraction region (+) and the avoidance region (−), and (4) particularly, a result comparable to a clinical result obtained by the method in related art in a cancer test is obtained, and thus, even in a case where the nematodes are imaged in a state where a plurality of nematodes overlap each other, the "taxis analysis value calculated by the calculation of the above expression (1) by the computer" does not deviate from the "taxis index calculated by manual counting".

Figure 20:
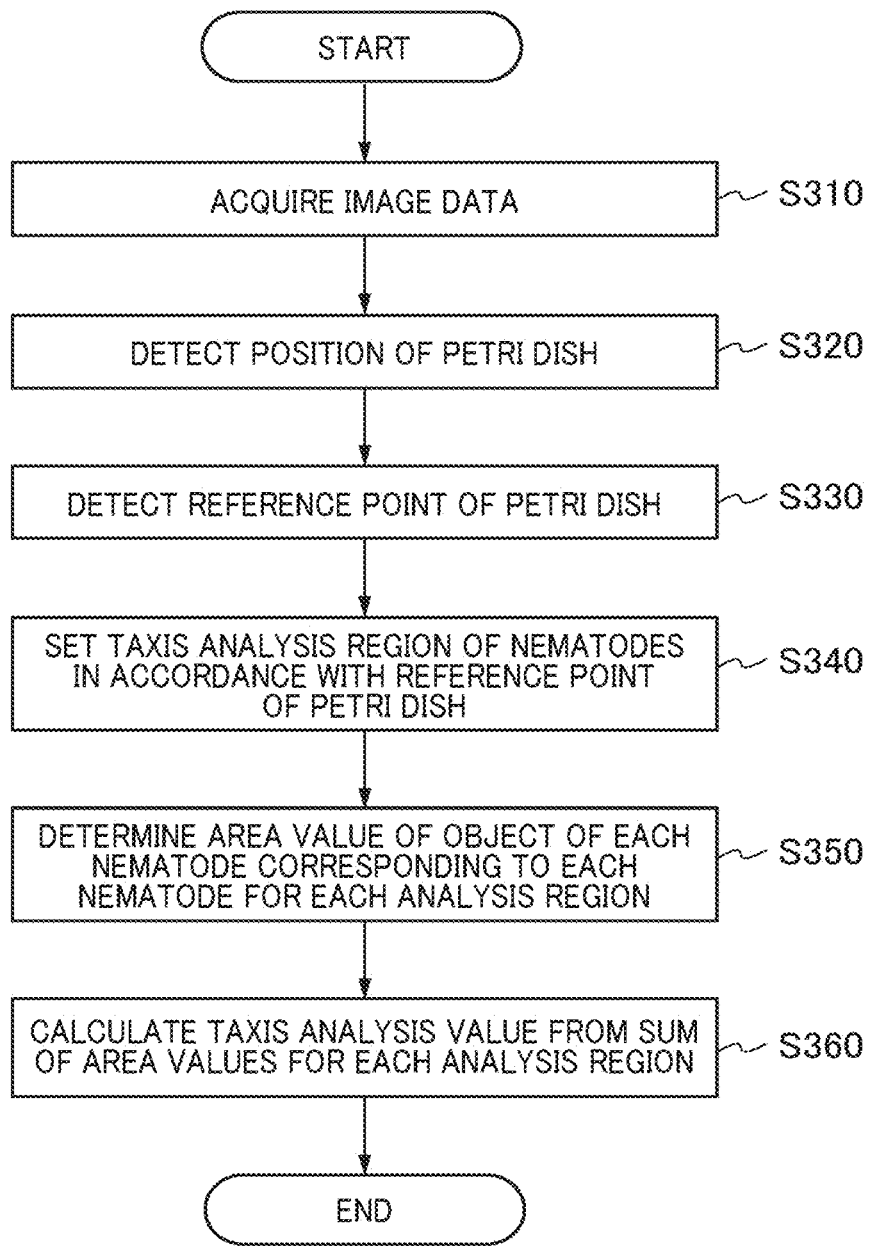
FIG. 20 is a flowchart illustrating an example of processing using a first method for calculating a taxis analysis value.

FIG. 20 is a flowchart illustrating an example of processing using the first calculation method of the taxis analysis value.

(Step S310) First, the camera control unit 31 controls the camera 15b to image the Petri dish 21 containing nematodes and stores image data obtained by the imaging in the storage 16. The image processing unit 32 acquires the image data.

(Step S320) Next, the image processing unit 32 detects the position of the Petri dish in the image data.

(Step S330) Next, the image processing unit 32 detects a reference point of the Petri dish in the image data.

(Step S340) Next, the image processing unit 32 sets the attraction region and the avoidance region of the nematodes in accordance with the reference point of the Petri dish. Here, the attraction region and the avoidance region are collectively referred to as a taxis analysis region.

(Step S350) Next, the analysis unit 33 determines an area value of an area occupied by an object of each nematode corresponding to each nematode (object of the nematode) for each attraction region and each avoidance region.

(Step S360) Next, the analysis unit 33 calculates a sum $S_A$ of the area values of the objects of the nematodes in the attraction region and a sum $S_B$ of the area values of the objects of the nematodes in the avoidance region and substitutes the calculated sum $S_A$ and the sum $S_B$ into expression (1) to calculate the taxis analysis value according to expression (1).

<Second Calculation Method>

Next, a second calculation method of the taxis analysis value of the present embodiment will be described. The second calculation method is a method in which the taxis analysis value is calculated using a peak in a histogram of area values of the objects of the nematodes.

Figure 21:
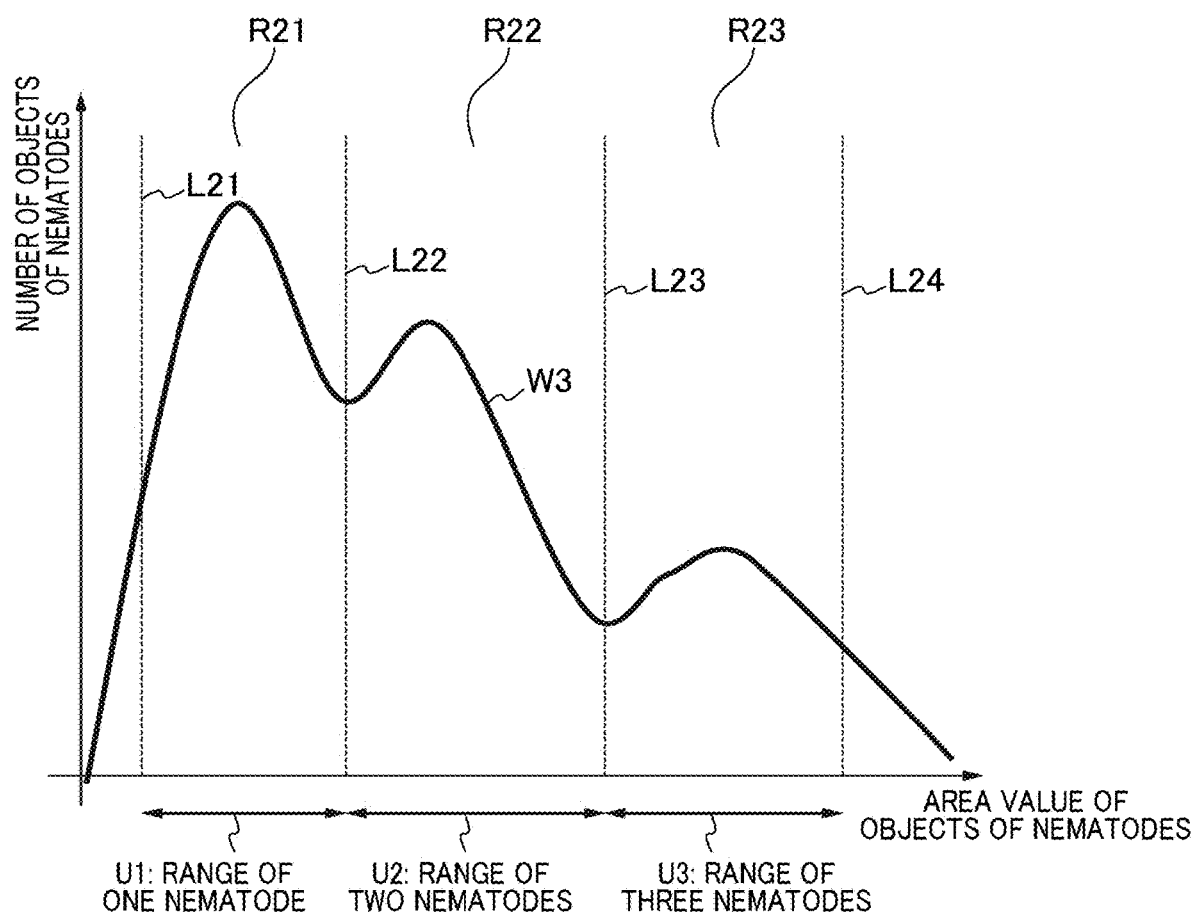
FIG. 21 is an example of a histogram of the number of objects of nematodes and area values of the objects of the nematodes in all taxis analysis regions (both the attraction region and the avoidance region).

FIG. 21 is an example of a histogram of the number of objects of nematodes and area values of the objects of the nematodes in all the taxis analysis regions (both the attraction region and the avoidance region). FIG. 21 illustrates a histogram W3 of the number of objects of the nematodes and area values of the objects of the nematodes in all the taxis analysis regions (both the attraction region and the avoidance region). In FIG. 21, an area range U1 of one nematode represents an area range of one nematode and is a range between a boundary line L21 and a boundary line L22. In addition, an area range U2 of two nematodes represents an area range in a case where two nematodes overlap and is a range between the boundary line L22 and a boundary line L23. In addition, an area range U3 of three nematodes represents an area range in a case where three nematodes overlap and is a range between the boundary line L23 and a boundary line L24.

It has been observed that an area value of a region where a plurality of nematodes overlap is larger than that of an object of one nematode, and a possible range of the area value varies for each number of overlapping nematodes. In the second calculation method, as illustrated in FIG. 21, for each of the regions R21, R22, and R23 including one maximum point, the area range (for example, the area range U1 in a case of one nematode, the area range U2 in a case of two nematode, and the area range U3 in a case of three nematodes) of the region occupied for each number of nematodes is set from the histogram of the number of objects of the nematodes and the area value of the objects of the nematodes as illustrated in FIG. 21. The number of objects of the nematodes is integrated for each set area range, and the taxis analysis value is calculated according to the following equation (2).

$$I=(N_A-N_B)/(N_A+N_B) \quad (2)$$

Here, I is a taxis analysis value, $N_A$ is a sum of "the number of nematodes assigned to the area range"×"the number of objects of the nematodes falling within the area range" in the attraction region, and $N_B$ is a sum of "the number of nematodes assigned to the area range"×"the number of objects of the nematodes falling within the area range" in the avoidance region. Note that only one of the attraction region and the avoidance region may be set, and the area value of the objects of the nematodes in the set region and the area value of the objects of the nematodes in the entire region of the Petri dish object OB12 may be used to perform taxis analysis. For example, in a case where the attraction region is set, the $N_B$ in the avoidance region can be regarded as a value obtained by subtracting the $N_A$ in the attraction region from the sum of "the number of nematodes assigned to the area range"×"the number of objects of the nematodes falling within the area range" in the entire region of the Petri dish object OB12.

In the second calculation method, (1) it has been observed that the distribution of the nematodes after the test is most in a state where one nematode is in a stationary state, and the number of states tends to be smaller in a state where a plurality of nematodes overlap each other as the number of overlaps increases, and (2) from the histogram of the area values of the objects of the nematodes in the attraction region (+) and the avoidance region (−), the overlapping state of one nematode, two nematodes, and three nematodes . . . can be predicted from a maximum point and a minimum point of the histogram. Thus, even in a case where the images of the nematodes overlap each other, the "taxis analysis value calculated by automatic calculation by the computer" does not deviate from the "taxis index calculated by manual counting".

Figure 22:
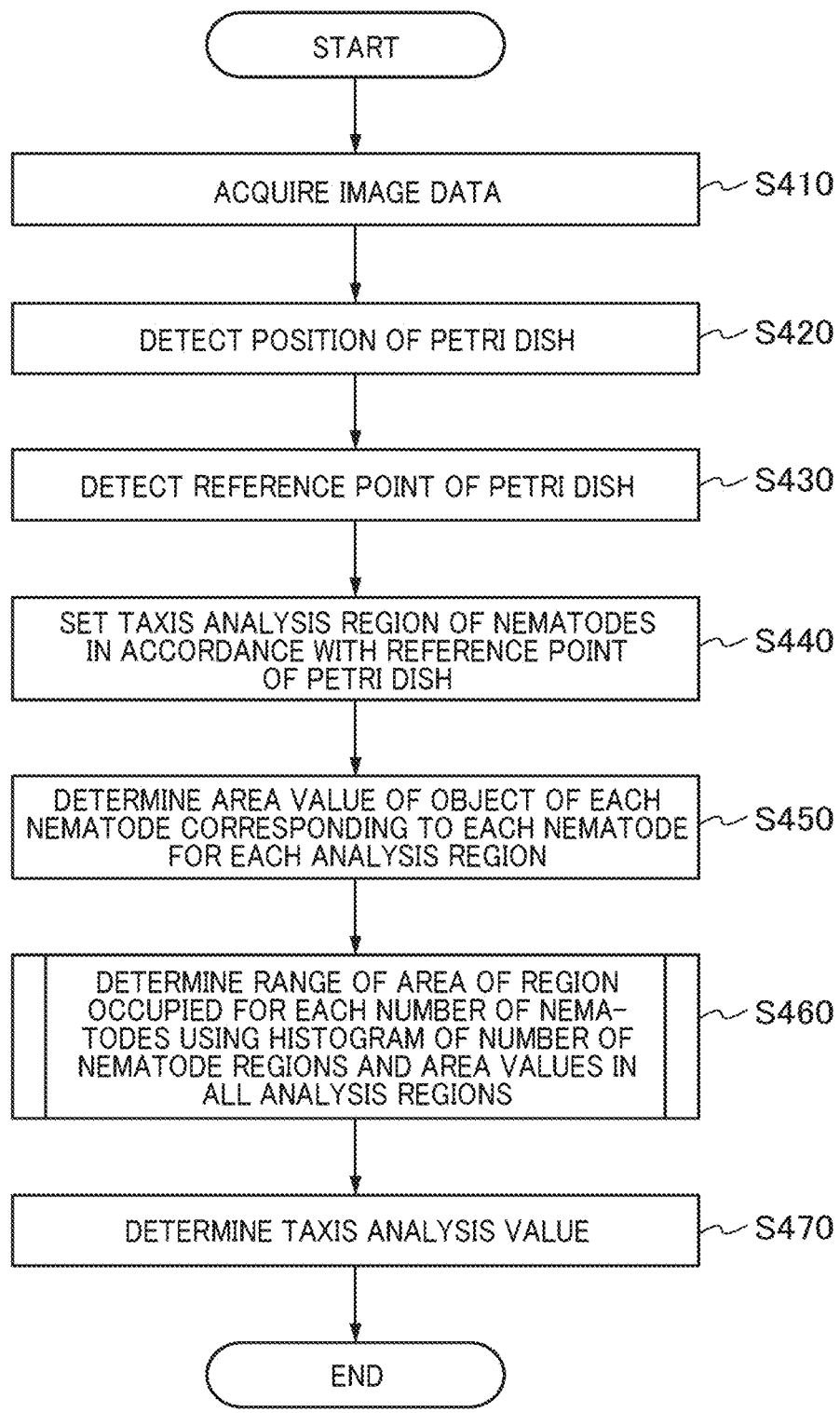
FIG. 22 is a flowchart illustrating an example of processing using a second method for calculating a taxis analysis value.

FIG. 22 is a flowchart illustrating an example of processing using the second calculation method of the taxis analysis value.

(Step S410) First, the camera control unit 31 controls the camera 15b to image the Petri dish 21 containing nematodes and stores image data obtained by the imaging in the storage 16. The image processing unit 32 acquires the image data.

(Step S420) Next, the image processing unit 32 detects the position of the Petri dish in the image data.

(Step S430) Next, the image processing unit 32 detects a reference point of the Petri dish in the image data.

(Step S440) Next, the image processing unit 32 sets the attraction region and the avoidance region of the nematodes in accordance with the reference point of the Petri dish.

(Step S450) Next, the analysis unit 33 determines the area value of the area occupied by each object of the nematode corresponding to each nematode for each attraction region and each avoidance region.

(Step S460) Next, the analysis unit 33 uses a histogram of the number of objects of the nematodes and the area value in the entire taxis analysis region (see FIG. 21) to determine the range of the area of the region occupied by each number of nematodes. Details of this processing will be described later with reference to FIG. 23.

(Step S470) Next, in each of the area ranges U1, U2, and U3 of the taxis analysis region (that is, each of the attraction region and the avoidance region), the number of objects of the nematodes falling within the area range is multiplied by the number of nematodes assigned to the area range, the sum of the multiplied values is calculated for each of the taxis analysis regions (that is, for each of the attraction region and the avoidance region), and the taxis analysis value is determined according to expression (2) using the sums $N_A$ and $N_B$ for each of the taxis analysis regions.

FIG. 23 is a flowchart illustrating an example of processing in step S460 of FIG. 22.

(Step S510) First, the analysis unit 33 obtains a maximum point and a minimum point of the histogram (see FIG. 21) of the number of objects of the nematodes and the area value in the entire taxis analysis region. Then, the index n is set to 1.

(Step S520) Next, the analysis unit 33 determines whether or not there is an n-th minimum point from the left.

(Step S530) In a case where it is determined in step S520 that there is the n-th minimum point from the left (step S520: Yes), the analysis unit 33 sets a lower limit of the area range of one nematode to a predetermined value when n=1. Here, the predetermined value is a value set for exclusion as noise of a small nematode that is not an adult, dust, or the like.

When n is equal to or greater than 2, the analysis unit 33 sets the lower limit of the area range of n nematodes to the x coordinate+1 at the (n−1)-th minimum point from the left of the histogram.

When n=1, assuming that Xmax1 is the x coordinate at the first maximum point from the left, the lower limit of the area value of one nematode may be set to Xmax1−(half width at half maximum of the first maximum point from the left).

(Step S540) The analysis unit 33 sets the x coordinate at the n-th minimum point from the left of the histogram as the upper limit of the area range of n nematodes. Then, the analysis unit 33 increases the index n by 1 and repeats the processing of step S520 and subsequent steps.

(Step S550) In a case where it is determined in step S520 that there is no n-th minimum point from the left (step S520: No), it is determined whether or not the upper limit of the area range of (n−1) nematodes is equal to or greater than the predetermined value.

(Step S560) In a case where the upper limit of the area range of (n−1) nematodes is equal to or greater than the predetermined value in step S550 (step S550: Yes), the analysis unit 33 does not set the upper limit of the area range of n nematodes (that is, the upper limit of the area range of n nematodes becomes equal to or greater than the lower limit of the area range of n nematodes). Note that the present invention is not limited thereto, and assuming that the x coordinate of the n-th maximum point is Xmaxn, the analysis unit 33 may set the upper limit of the area range of n nematodes to Xmaxn+(half width at half maximum of the n-th maximum point from the left).

(Step S570) In a case where the upper limit of the area range of (n−1) nematodes is not equal to or greater than the predetermined value in step S550, that is, less than the predetermined value (step S550: No), the analysis unit 33 sets the upper limit of the area range of n nematodes to the predetermined value.

Note that at least part of the control unit 14 and the analysis unit 17 described in the above-described embodiments may be configured by hardware or software. A program for implementing at least part of the functions of the analysis unit 17 may be stored in a recording medium such as a flexible disk and a CD-ROM and may be read and executed by a computer. The recording medium is not limited to a removable recording medium such as a magnetic disk and an optical disk and may be a fixed recording medium such as a hard disk device or a memory.

In addition, a program that implements at least part of the functions of the control unit 14 and the analysis unit 17 may be distributed via a communication line (including wireless communication) such as the Internet. Further, the program may be distributed via a wired line or a wireless line such as the Internet or stored in a recording medium in an encrypted, modulated, or compressed state.

Furthermore, the control unit 14 and the analysis unit 17 may be caused to function by one or a plurality of information processing devices. In a case of using a plurality of information processing devices, one of the information processing devices may be a computer, and the function may be implemented as at least one unit of the analysis unit 17 by the computer executing a predetermined program.

In the invention of the method, all the processes (steps) may be implemented by automatic control by a computer. In addition, each process may be implemented by a computer while progress of the processes is manually controlled. Furthermore, at least part of all processes may be manually performed.

As described above, the present invention is not limited to the above-described embodiments as they are and can be embodied by modifying the components without departing from the gist of the present invention in the implementation stage. In addition, various inventions can be formed by appropriately combining a plurality of components disclosed in the above embodiments. For example, some components may be deleted from all the components described in the embodiments. Furthermore, components in different embodiments may be appropriately combined.

REFERENCE SIGNS LIST 1 taxis analysis system
10, 10b processor
11 container supply unit
111 supply conveyor
112 supply robot
12 stationary table
13 container take-out unit
131 take-out robot
132 container conveyance unit
1321 arm
133 lid removal unit
1331 robot hand
134 sensor
14 control unit
15 imaging unit
151 support column
152 base member
153 light source
16 storage
161 image database
162 inspection database
17 analysis unit
21, 21b petri dish
22 lid
3 taxis analysis device
31 camera control unit
32 image processing unit
33 analysis unit

The invention claimed is:

1. A taxis analysis method for performing taxis analysis of nematodes using a container in which a reference point is provided in the container or a culture medium in the container, the taxis analysis method comprising:

imaging a distribution mode of the nematodes in the container;

detecting a position of a reference point object, corresponding to the reference point, included in an image obtained by the imaging;

determining an attraction region and/or an avoidance region in the image based on the detected position of the reference point object included in the image; and executing taxis analysis using objects of nematodes in the determined attraction region and/or the avoidance region, wherein the determining of the attraction region and/or the avoidance region further comprises:

detecting a center of a container object corresponding to the container included in the image, determining, in the image, an angle of a straight line passing through both the position of the reference point object and the center of the container object with respect to a reference line; and one of (1) rotating a reference format in which the attraction region and/or the avoidance region is set in advance with respect to the reference line by the angle, and superimposing the rotated reference format on the image to determine the attraction region and/or the avoidance region in the image; (2) rotating the image by the angle to determine the attraction region and/or the avoidance region in the rotated image; and (3) rotating the container by the angle, imaging a distribution mode of the nematodes in the container after the rotation to obtain a second image, and determining the attraction region and/or the avoidance region by comparing the second image with a reference format in which the attraction region and/or the avoidance region is set in advance with respect to the reference line.

2. The taxis analysis method according to claim 1, wherein the executing of the taxis analysis further comprises counting the nematodes in the determined attraction region and/or the nematodes in the determined avoidance region, and outputting a taxis analysis result according to a count result.

3. The taxis analysis method according to claim 1,
wherein the reference point is a code including particular container identification information identifying the container, the image obtained in the imaging includes a code object corresponding to the code, and the taxis analysis method further comprises:
reading the particular container identification information from the code object; and
storing, in a storage, a taxis analysis result that is a result of executing the taxis analysis in association with the read container identification information.

4. The taxis analysis method according to claim 3,
wherein subject identification information identifying a subject and container identification information are stored in the storage in association with each other, and
the taxis analysis method further comprises identifying subject identification information corresponding to the particular container identification information read from the code object with reference to the storage.

5. The taxis analysis method according to claim 1, wherein the reference point comprises a first reference point and/or a second reference point.

6. The taxis analysis method according to claim 1, further comprising removing a lid of the container before imaging an inside of the container.

7. A cancer evaluation method comprising:
performing the taxis analysis method according to claim 1 to obtain a taxis analysis result; and
evaluating a possibility of cancer in a subject using the taxis analysis result obtained.

8. A taxis analysis system for performing taxis analysis of nematodes using a container in which a reference point is provided in the container or a culture medium in the container, the taxis analysis system comprising:

control circuitry configured to control an imaging unit to image a distribution mode of the nematodes in the container; and analysis circuitry configured to detect a position of a reference point object corresponding to the reference point included in an image obtained by the imaging unit, determine an attraction region and/or an avoidance region in the image based on the detected position, and execute taxis analysis using objects of nematodes in the determined attraction region and/or avoidance region, wherein the analysis circuitry is further configured to determine of the attraction region and/or the avoidance region by:

detecting a center of a container object corresponding to the container included in the image, determining, in the image, an angle of a straight line passing through both the position of the reference point object and the center of the container object with respect to a reference line; and one of (1) rotating a reference format in which the attraction region and/or the avoidance region is set in advance with respect to the reference line by the angle, and superimposing the rotated reference format on the image to determine the attraction region and/or the avoidance region in the image; (2) rotating the image by the angle to determine the attraction region and/or the avoidance region in the rotated image; and (3) rotating the container by the angle, imaging a distribution mode of the nematodes in the container after the rotation to obtain a second image, and determining the attraction region and/or the avoidance region by comparing the second image with a reference format in which the attraction region and/or the avoidance region is set in advance with respect to the reference line.

9. A taxis analysis method for performing taxis analysis of nematodes, the taxis analysis method comprising:

imaging a distribution mode of nematodes in a container;

extracting a region occupied by objects of nematodes corresponding to the nematodes included in an image obtained by the imaging;

executing taxis analysis using an area value of the extracted region in an attraction region and/or an avoidance region in the image, wherein the executing step comprises determining of the attraction region and/or the avoidance region by:

detecting a center of a container object corresponding to the container included in the image, determining, in the image, an angle of a straight line passing through both a position of a reference point object and the center of the container object with respect to a reference line; and one of (1) rotating a reference format in which the attraction region and/or the avoidance region is set in advance with respect to the reference line by the angle, and superimposing the rotated reference format on the image to determine the attraction region and/or the avoidance region in the image; (2) rotating the image by the angle to determine the attraction region and/or the avoidance region in the rotated image; and (3) rotating the container by the angle, imaging a distribution mode of the nematodes in the container after the rotation to obtain a second image, and determining the attraction region and/or the avoidance region by comparing the second image with a reference format in which the attraction region and/or the avoidance region is set in advance with respect to the reference line.

10. A cancer evaluation method comprising:
performing the taxis analysis method according to claim 9 to obtain a taxis analysis result; and
evaluating a possibility of cancer in a subject by using the taxis analysis result obtained.

* * * * *